United States Patent
Landrigan et al.

(10) Patent No.: US 9,642,956 B2
(45) Date of Patent: May 9, 2017

(54) APPARATUS AND METHOD FOR SEPARATING AND CONCENTRATING FLUIDS CONTAINING MULTIPLE COMPONENTS

(75) Inventors: Matthew D. Landrigan, Fort Wayne, IN (US); Matthew Swift, Fort Wayne, IN (US)

(73) Assignee: BIOMET BIOLOGICS, LLC, Warsaw, IN (US)

( * ) Notice: Subject to any disclaimer, the term of this patent is extended or adjusted under 35 U.S.C. 154(b) by 716 days.

(21) Appl. No.: 13/595,461

(22) Filed: Aug. 27, 2012

(65) Prior Publication Data

US 2014/0054246 A1 Feb. 27, 2014

(51) Int. Cl.
*B01L 3/00* (2006.01)
*B01D 21/26* (2006.01)
*A61M 1/36* (2006.01)
*A61M 1/02* (2006.01)
(Continued)

(52) U.S. Cl.
CPC .......... *A61M 1/029* (2013.01); *A61M 1/3693* (2013.01); *B01D 17/0217* (2013.01); *B01D 21/262* (2013.01); *B01L 3/50215* (2013.01); *B01L 9/06* (2013.01); *B01D 2221/10* (2013.01); *B01L 2400/0409* (2013.01); *B01L 2400/0478* (2013.01); *B01L 2400/0605* (2013.01); *B01L 2400/0638* (2013.01)

(58) Field of Classification Search
CPC ...... B01L 3/50; B01L 3/5021; B01L 3/50215; B01L 3/5082; B01L 3/50825; B01L 3/567; B01L 9/06; G01N 21/07; B01D 21/262; B01D 2201/16; B01D 2201/165; B01D 2201/167
See application file for complete search history.

(56) References Cited

U.S. PATENT DOCUMENTS 280,820 A 7/1883 Hickson et al.
593,333 A 11/1897 Park
(Continued)

FOREIGN PATENT DOCUMENTS

AU 696278 1/1999
BR 9103724 3/1993
(Continued)

OTHER PUBLICATIONS

245 Series Swabable Valves, Halkey Roberts, Jan. 2015, pp. 1.*
(Continued)

*Primary Examiner* — David C Mellon
(74) *Attorney, Agent, or Firm* — Schwegman Lundberg & Woessner, P.A.

(57) ABSTRACT

A buoy or float can be positioned within a separation container to assist in a physical separation of components of a whole material positioned in the separation container. The buoy can be positioned within the container to move from between and separation a first end and a second end of the container substantially unaffected by a portion of the whole material, including a clotted portion thereof. A first port can be provided near the first end of the container for introduction of the whole material and a second port can be provided near the second end of the container for removal of at least a portion of a separated material.

17 Claims, 8 Drawing Sheets

(51) Int. Cl.
*B01D 17/02* (2006.01)
*B01L 9/06* (2006.01)

(56) References Cited

U.S. PATENT DOCUMENTS

| | | | |
|---|---|---|---|
| 657,440 A * | 9/1900 | McCaw | A61M 5/204 27/24.2 |
| 1,468,313 A | 9/1923 | Lux | |
| 1,593,814 A | 7/1926 | Vogel | |
| 2,722,257 A | 11/1955 | Lockhart | |
| 3,013,557 A | 12/1961 | Pallotta | |
| 3,141,846 A | 7/1964 | Laven, Jr. | |
| 3,159,159 A | 12/1964 | Cohen | |
| 3,300,051 A | 1/1967 | Mitchell | |
| 3,409,165 A | 11/1968 | Creith | |
| 3,420,374 A | 1/1969 | Umeda | |
| 3,441,143 A | 4/1969 | Kudlaty | |
| 3,453,364 A | 7/1969 | Flodin et al. | |
| 3,469,369 A | 9/1969 | Helmke | |
| 3,508,653 A | 4/1970 | Coleman | |
| 3,545,671 A | 12/1970 | Ross | |
| 3,583,627 A | 6/1971 | Wilson | |
| 3,596,652 A | 8/1971 | Winkelman | |
| 3,647,070 A | 3/1972 | Adler | |
| 3,654,925 A | 4/1972 | Holderith | |
| 3,661,265 A | 5/1972 | Greenspan | |
| 3,706,305 A | 12/1972 | Berger et al. | |
| 3,706,306 A | 12/1972 | Berger et al. | |
| 3,723,244 A | 3/1973 | Breillatt, Jr. | |
| 3,741,400 A | 6/1973 | Dick | |
| 3,779,383 A | 12/1973 | Ayres | |
| 3,785,549 A | 1/1974 | Latham, Jr. | |
| 3,814,248 A | 6/1974 | Lawhead | |
| 3,849,072 A | 11/1974 | Ayres | |
| 3,850,369 A | 11/1974 | Bull et al. | |
| 3,879,295 A | 4/1975 | Glover et al. | |
| 3,887,466 A | 6/1975 | Ayres | |
| 3,894,952 A | 7/1975 | Ayres | |
| 3,896,733 A | 7/1975 | Rosenberg | |
| 3,897,337 A | 7/1975 | Ayres | |
| 3,897,343 A | 7/1975 | Ayres | |
| 3,909,419 A | 9/1975 | Ayres | |
| 3,929,646 A | 12/1975 | Adler | |
| 3,931,010 A | 1/1976 | Ayres et al. | |
| 3,931,018 A | 1/1976 | North, Jr. | |
| 3,935,113 A | 1/1976 | Ayres | |
| 3,937,211 A | 2/1976 | Merten | |
| 3,941,699 A | 3/1976 | Ayres | |
| 3,945,928 A | 3/1976 | Ayres | |
| 3,951,801 A | 4/1976 | Ayres | |
| 3,957,654 A | 5/1976 | Ayres | |
| 3,962,085 A | 6/1976 | Liston et al. | |
| 3,965,889 A | 6/1976 | Sachs | |
| 3,972,812 A | 8/1976 | Gresl, Jr. | |
| 3,982,691 A | 9/1976 | Schlutz | |
| 4,001,122 A | 1/1977 | Griffin | |
| 4,020,831 A | 5/1977 | Adler | |
| 4,046,699 A | 9/1977 | Zine, Jr. | |
| 4,055,501 A | 10/1977 | Cornell | |
| 4,059,108 A | 11/1977 | Latham, Jr. | |
| 4,066,549 A | 1/1978 | Oeser et al. | |
| 4,077,396 A | 3/1978 | Wardlaw et al. | |
| 4,088,582 A | 5/1978 | Murty et al. | |
| 4,146,172 A | 3/1979 | Cullis et al. | |
| 4,152,270 A | 5/1979 | Cornell | |
| 4,154,690 A | 5/1979 | Ballies et al. | |
| 4,159,896 A | 7/1979 | Levine et al. | |
| 4,187,979 A | 2/1980 | Cullis et al. | |
| 4,189,385 A | 2/1980 | Greenspan | |
| 4,203,840 A | 5/1980 | Stoeppler et al. | |
| 4,204,537 A | 5/1980 | Latham, Jr. | |
| 4,225,580 A | 9/1980 | Rothman et al. | |
| 4,229,298 A | 10/1980 | Bange | |
| 4,269,718 A | 5/1981 | Persidsky | |
| 4,294,707 A | 10/1981 | Ikeda et al. | |
| 4,298,598 A | 11/1981 | Schwarz et al. | |
| 4,300,717 A | 11/1981 | Latham, Jr. | |
| 4,303,193 A | 12/1981 | Latham, Jr. | |
| 4,314,823 A | 2/1982 | Rich, Jr. et al. | |
| 4,322,298 A | 3/1982 | Persidsky | |
| 4,332,351 A | 6/1982 | Kellogg et al. | |
| 4,362,567 A | 12/1982 | Schwarz et al. | |
| 4,364,832 A | 12/1982 | Ballies et al. | |
| 4,377,572 A | 3/1983 | Schwarz et al. | |
| 4,379,849 A | 4/1983 | Heimreid | |
| 4,411,794 A | 10/1983 | Schwinn et al. | |
| 4,414,976 A | 11/1983 | Schwarz et al. | |
| 4,416,654 A | 11/1983 | Schoendorfer et al. | |
| 4,417,981 A | 11/1983 | Nugent | |
| 4,424,132 A | 1/1984 | Iriguchi | |
| 4,427,650 A | 1/1984 | Stroetmann et al. | |
| 4,427,651 A | 1/1984 | Stroetmann et al. | |
| 4,442,655 A | 4/1984 | Stroetmann | |
| 4,443,345 A | 4/1984 | Wells | |
| 4,445,550 A | 5/1984 | Davis et al. | |
| 4,446,021 A | 5/1984 | Aufderhaar et al. | |
| 4,453,927 A | 6/1984 | Sinko | |
| 4,453,939 A | 6/1984 | Zimmerman et al. | |
| 4,464,167 A | 8/1984 | Schoendorfer et al. | |
| 4,511,662 A | 4/1985 | Baran et al. | |
| 4,537,767 A | 8/1985 | Rothman et al. | |
| RE32,089 E | 3/1986 | Blatt et al. | |
| 4,577,514 A | 3/1986 | Bradley et al. | |
| 4,610,656 A | 9/1986 | Mortensen | |
| 4,617,009 A | 10/1986 | Ohlin et al. | |
| 4,627,879 A | 12/1986 | Rose et al. | |
| 4,631,055 A | 12/1986 | Redl et al. | |
| 4,632,761 A | 12/1986 | Bowers et al. | |
| 4,639,316 A | 1/1987 | Eldegheidy | |
| 4,650,678 A | 3/1987 | Fuhge et al. | |
| 4,655,211 A | 4/1987 | Sakamoto et al. | |
| 4,672,969 A | 6/1987 | Dew | |
| 4,675,117 A | 6/1987 | Neumann et al. | |
| 4,680,025 A | 7/1987 | Kruger et al. | |
| 4,714,457 A | 12/1987 | Alterbaum | |
| 4,722,790 A | 2/1988 | Cawley et al. | |
| 4,724,317 A | 2/1988 | Brown et al. | |
| 4,735,616 A | 4/1988 | Eibl et al. | |
| 4,735,726 A | 4/1988 | Duggins | |
| 4,738,655 A | 4/1988 | Brimhall et al. | |
| 4,755,300 A | 7/1988 | Fischel et al. | |
| 4,755,301 A | 7/1988 | Bowers | |
| 4,770,779 A | 9/1988 | Ichikawa et al. | |
| 4,776,964 A | 10/1988 | Schoendorfer et al. | |
| 4,818,291 A | 4/1989 | Iwatsuki et al. | |
| 4,818,386 A | 4/1989 | Burns | |
| 4,828,710 A | 5/1989 | Itoh et al. | |
| 4,832,851 A | 5/1989 | Bowers et al. | |
| 4,834,890 A | 5/1989 | Brown et al. | |
| 4,839,058 A | 6/1989 | Cawley et al. | |
| 4,844,818 A | 7/1989 | Smith | |
| 4,846,780 A | 7/1989 | Galloway et al. | |
| 4,846,835 A | 7/1989 | Grande | |
| 4,850,952 A | 7/1989 | Figdor et al. | |
| 4,853,137 A | 8/1989 | Ersson | |
| 4,871,462 A | 10/1989 | Fischel et al. | |
| 4,874,368 A | 10/1989 | Miller et al. | |
| 4,877,520 A | 10/1989 | Burns | |
| 4,879,031 A | 11/1989 | Panzani et al. | |
| 4,900,453 A | 2/1990 | Sedlmayer et al. | |
| 4,902,281 A | 2/1990 | Avoy | |
| 4,909,251 A | 3/1990 | Seelich | |
| 4,915,847 A | 4/1990 | Dillon et al. | |
| 4,917,801 A | 4/1990 | Luderer et al. | |
| 4,928,603 A | 5/1990 | Rose et al. | |
| 4,929,242 A | 5/1990 | Desecki et al. | |
| 4,933,291 A | 6/1990 | Daiss et al. | |
| 4,939,081 A | 7/1990 | Figdor et al. | |
| 4,943,273 A | 7/1990 | Pages et al. | |
| 4,946,601 A | 8/1990 | Fiehler | |
| 4,950,220 A | 8/1990 | Wells et al. | |
| 4,957,637 A | 9/1990 | Cornell | |
| 4,957,638 A | 9/1990 | Smith | |
| 4,973,168 A | 11/1990 | Chan | |

(56) References Cited

U.S. PATENT DOCUMENTS

| | | |
|---|---|---|
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,024,613 A | 6/1991 | Vasconcellos et al. |
| 5,030,215 A | 7/1991 | Morse et al. |
| 5,030,341 A | 7/1991 | McEwen et al. |
| 5,039,401 A | 8/1991 | Columbus et al. |
| 5,045,048 A | 9/1991 | Kaleskas et al. |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,178,602 A | 1/1993 | Wells |
| 5,185,001 A | 2/1993 | Galanakis |
| 5,188,583 A | 2/1993 | Guigan et al. |
| 5,190,057 A | 3/1993 | Sarfarazi |
| 5,190,759 A | 3/1993 | Lindblad et al. |
| 5,197,985 A | 3/1993 | Caplan et al. |
| 5,203,825 A | 4/1993 | Haynes et al. |
| 5,204,537 A | 4/1993 | Bennet et al. |
| 5,206,023 A | 4/1993 | Hunziker |
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,251,786 A | 10/1993 | Sarrine |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,354,483 A | 10/1994 | Furse |
| 5,360,413 A * | 11/1994 | Leason et al. ............... 604/249 |
| 5,370,221 A | 12/1994 | Magnusson et al. |
| 5,370,802 A | 12/1994 | Brown |
| 5,372,945 A | 12/1994 | Alchas et al. |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,409,833 A | 4/1995 | Hu et al. |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,480,378 A | 1/1996 | Weis-Fogh et al. |
| 5,484,383 A | 1/1996 | Fitch, Jr. et al. |
| 5,486,359 A | 1/1996 | Caplan et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,505,685 A | 4/1996 | Antwiler |
| 5,510,102 A | 4/1996 | Cochrum |
| 5,520,885 A | 5/1996 | Coelho et al. |
| 5,525,477 A | 6/1996 | Hassouna |
| 5,533,518 A | 7/1996 | Vogler |
| 5,560,830 A | 10/1996 | Coleman et al. |
| 5,575,778 A | 11/1996 | Hardt et al. |
| 5,577,513 A | 11/1996 | Van Vlasselaer |
| 5,585,007 A | 12/1996 | Antanavich et al. |
| 5,588,958 A | 12/1996 | Cunningham et al. |
| 5,589,462 A | 12/1996 | Patat et al. |
| 5,601,711 A | 2/1997 | Sklar et al. |
| 5,601,727 A | 2/1997 | Bormann et al. |
| 5,603,845 A | 2/1997 | Holm |
| 5,607,579 A | 3/1997 | Latham, Jr. et al. |
| 5,614,106 A | 3/1997 | Payrat et al. |
| 5,618,663 A | 4/1997 | Delmas et al. |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh et al. |
| 5,643,193 A | 7/1997 | Papillon et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Levine |
| 5,716,616 A | 2/1998 | Prockop et al. |
| 5,723,331 A | 3/1998 | Tubo et al. |
| 5,724,988 A | 3/1998 | Dennehey et al. |
| 5,733,466 A | 3/1998 | Benebo et al. |
| 5,733,545 A | 3/1998 | Hood, III |
| 5,736,033 A | 4/1998 | Coleman et al. |
| 5,738,784 A | 4/1998 | Holm et al. |
| 5,738,796 A | 4/1998 | Bormann et al. |
| 5,750,025 A | 5/1998 | Holmes et al. |
| 5,750,658 A | 5/1998 | Coelho et al. |
| 5,762,798 A | 6/1998 | Wenthold et al. |
| 5,785,700 A | 7/1998 | Olson |
| 5,786,217 A | 7/1998 | Tubo et al. |
| 5,788,662 A | 8/1998 | Antanavich et al. |
| 5,792,344 A | 8/1998 | Holm |
| 5,795,489 A | 8/1998 | Holm et al. |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |
| 5,817,519 A | 10/1998 | Zelmanovic et al. |
| 5,823,986 A | 10/1998 | Peterson |
| 5,824,084 A * | 10/1998 | Muschler ............... A61L 27/32 128/898 |
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,853,600 A | 12/1998 | McNeal et al. |
| 5,860,937 A | 1/1999 | Cohen |

(56) References Cited

U.S. PATENT DOCUMENTS

| | | |
|---|---|---|
| 5,863,892 A | 1/1999 | Stern et al. |
| 5,865,785 A | 2/1999 | Bischof |
| 5,885,239 A | 3/1999 | Headley et al. |
| 5,889,584 A | 3/1999 | Wardlaw |
| 5,895,346 A | 4/1999 | Wells et al. |
| 5,899,874 A | 5/1999 | Jonsson et al. |
| 5,900,245 A | 5/1999 | Sawhney et al. |
| 5,906,934 A | 5/1999 | Grande et al. |
| 5,916,557 A | 6/1999 | Berlowitz-Tarrant et al. |
| 5,916,743 A | 6/1999 | Lake et al. |
| 5,918,622 A | 7/1999 | Perez et al. |
| 5,924,972 A | 7/1999 | Turvaville et al. |
| 5,934,803 A | 8/1999 | Hutter |
| 5,938,621 A | 8/1999 | Kelly et al. |
| 5,951,160 A | 9/1999 | Ronk |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm et al. |
| 5,961,210 A | 10/1999 | McCardel et al. |
| 5,980,734 A | 11/1999 | Itoh et al. |
| 5,980,757 A | 11/1999 | Brown et al. |
| 5,985,315 A | 11/1999 | Patat et al. |
| 5,997,544 A | 12/1999 | Nies et al. |
| 6,007,811 A | 12/1999 | Sawyer et al. |
| 6,010,627 A | 1/2000 | Hood, III |
| 6,011,490 A | 1/2000 | Tonnesen et al. |
| 6,020,196 A | 2/2000 | Hu et al. |
| 6,022,306 A | 2/2000 | Dumont et al. |
| 6,025,201 A | 2/2000 | Zelmanovic et al. |
| 6,027,655 A | 2/2000 | Holm |
| 6,049,026 A | 4/2000 | Muschler |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,089,541 A * | 7/2000 | Weinheimer et al. ..... 251/149.6 |
| 6,090,793 A | 7/2000 | Zimmermann et al. |
| 6,096,309 A | 8/2000 | Prior et al. |
| 6,102,843 A | 8/2000 | Kelley et al. |
| 6,117,425 A | 9/2000 | MacPhee et al. |
| 6,123,655 A | 9/2000 | Fell et al. |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,200,606 B1 | 3/2001 | Peterson et al. |
| 6,214,338 B1 | 4/2001 | Antanavich et al. |
| 6,221,315 B1 | 4/2001 | Giesler et al. |
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,286,670 B1 | 9/2001 | Smith |
| 6,296,602 B1 | 10/2001 | Headley |
| 6,316,247 B1 | 11/2001 | Katz et al. |
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,334,842 B1 | 1/2002 | Hlavinka et al. |
| 6,342,157 B1 | 1/2002 | Hood, III |
| 6,351,659 B1 | 2/2002 | Vilsmeier |
| 6,355,239 B1 | 3/2002 | Bruder et al. |
| 6,368,298 B1 | 4/2002 | Beretta et al. |
| 6,368,498 B1 | 4/2002 | Guilmette |
| 6,398,972 B1 | 6/2002 | Blasetti et al. |
| 6,406,671 B1 | 6/2002 | DiCesare et al. |
| 6,409,528 B1 | 6/2002 | Bodnar |
| 6,410,344 B1 | 6/2002 | Chung et al. |
| 6,417,004 B1 | 7/2002 | Brady et al. |
| 6,440,444 B2 | 8/2002 | Boyce et al. |
| 6,444,228 B1 | 9/2002 | Baugh et al. |
| 6,464,624 B2 | 10/2002 | Pages |
| 6,471,069 B2 | 10/2002 | Lin et al. |
| 6,472,162 B1 | 10/2002 | Coelho et al. |
| 6,487,992 B1 | 12/2002 | Hollis |
| 6,508,778 B1 | 1/2003 | Verkaart et al. |
| 6,516,953 B1 | 2/2003 | DiCesare et al. |
| 6,523,698 B1 | 2/2003 | Dennehey et al. |
| 6,544,162 B1 | 4/2003 | Van Wie et al. |
| 6,544,727 B1 | 4/2003 | Hei |
| 6,558,341 B1 | 5/2003 | Swisher |
| 6,563,953 B2 | 5/2003 | Lin et al. |
| 6,596,180 B2 | 7/2003 | Baugh et al. |
| 6,623,959 B2 | 9/2003 | Harris |
| 6,629,919 B2 | 10/2003 | Egozy et al. |
| 6,638,503 B2 | 10/2003 | Chitte et al. |
| 6,676,629 B2 | 1/2004 | Andrew et al. |
| 6,716,187 B1 | 4/2004 | Jorgensen et al. |
| 6,719,901 B2 | 4/2004 | Dolecek et al. |
| 6,733,471 B1 | 5/2004 | Ericson et al. |
| 6,758,978 B1 | 7/2004 | Bedell |
| 6,764,531 B2 | 7/2004 | Hogan |
| 6,777,231 B1 | 8/2004 | Katz et al. |
| 6,803,022 B2 | 10/2004 | DiCesare et al. |
| 6,811,777 B2 | 11/2004 | Mishra |
| 6,830,762 B2 | 12/2004 | Baugh et al. |
| 6,835,353 B2 | 12/2004 | Smith et al. |
| 6,835,377 B2 | 12/2004 | Goldberg et al. |
| RE38,730 E | 4/2005 | Wells et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Wells et al. |
| 6,979,307 B2 | 12/2005 | Beretta et al. |
| 7,011,644 B1 | 3/2006 | Andrew et al. |
| 7,077,273 B2 | 7/2006 | Ellsworth et al. |
| 7,077,827 B2 | 7/2006 | Greenfield |
| 7,155,288 B2 | 12/2006 | Soykan et al. |
| 7,179,391 B2 | 2/2007 | Leach et al. |
| 7,195,606 B2 | 3/2007 | Ballin |
| 7,223,346 B2 | 5/2007 | Dorian et al. |
| 7,273,886 B2 | 9/2007 | Olivero et al. |
| 7,354,515 B2 | 4/2008 | Coull et al. |
| 7,374,678 B2 | 5/2008 | Leach et al. |
| 7,411,006 B2 | 8/2008 | Shanbrom |
| 7,470,371 B2 | 12/2008 | Dorian et al. |
| 7,531,355 B2 | 5/2009 | Rodriguez et al. |
| 7,553,413 B2 | 6/2009 | Dorian et al. |
| 7,694,828 B2 | 4/2010 | Swift et al. |
| 7,806,276 B2 | 10/2010 | Leach et al. |
| 7,845,499 B2 | 12/2010 | Higgins et al. |
| 7,901,584 B2 | 3/2011 | Dorian et al. |
| 7,914,689 B2 | 3/2011 | Higgins et al. |
| 7,987,995 B2 | 8/2011 | Dorian et al. |
| 8,048,321 B2 | 11/2011 | Leach et al. |
| 8,062,534 B2 | 11/2011 | Higgins et al. |
| 8,067,534 B2 | 11/2011 | Jagota et al. |
| 8,567,609 B2 | 10/2013 | Landrigan et al. |
| 8,596,470 B2 | 12/2013 | Leach et al. |
| 8,783,470 B2 | 7/2014 | Hecker et al. |
| 8,801,586 B2 | 8/2014 | Dorian et al. |
| 8,808,551 B2 | 8/2014 | Leach et al. |
| 8,950,586 B2 | 2/2015 | Dorian et al. |
| 8,992,862 B2 | 3/2015 | Leach et al. |
| 9,011,800 B2 | 4/2015 | Leach et al. |
| 2001/0009757 A1 | 7/2001 | Bischof et al. |
| 2002/0032112 A1 | 3/2002 | Pages |
| 2002/0035820 A1 | 3/2002 | Farris |
| 2002/0076400 A1 | 6/2002 | Katz et al. |
| 2002/0082220 A1 | 6/2002 | Hoemann et al. |
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0161449 A1 | 10/2002 | Muschler |
| 2002/0169408 A1 | 11/2002 | Beretta et al. |

(56) References Cited

U.S. PATENT DOCUMENTS

| | | |
|---|---|---|
| 2002/0172666 A1 | 11/2002 | Sacchi et al. |
| 2002/0182664 A1 | 12/2002 | Dolecek et al. |
| 2002/0192632 A1 | 12/2002 | Hei et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |
| 2003/0082152 A1 | 5/2003 | Hedrick et al. |
| 2003/0185803 A1 | 10/2003 | Kadiyala et al. |
| 2003/0191429 A1 | 10/2003 | Andrew et al. |
| 2003/0205538 A1 | 11/2003 | Dorian et al. |
| 2004/0005246 A1 | 1/2004 | Efthimiadis et al. |
| 2004/0013575 A1 | 1/2004 | Stevens et al. |
| 2004/0120942 A1 | 6/2004 | McGinnis et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2004/0251217 A1 | 12/2004 | Leach et al. |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0109716 A1 | 5/2005 | Leach et al. |
| 2005/0130301 A1 | 6/2005 | McKay et al. |
| 2005/0145187 A1 | 7/2005 | Gray |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0196393 A1 | 9/2005 | Shanbrom |
| 2005/0196874 A1 | 9/2005 | Dorian et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0051865 A1 | 3/2006 | Higgins et al. |
| 2006/0057693 A1 | 3/2006 | Simon |
| 2006/0083720 A1 | 4/2006 | Fraser et al. |
| 2006/0140923 A1 | 6/2006 | Evangelista et al. |
| 2006/0151384 A1 | 7/2006 | Ellsworth et al. |
| 2006/0175242 A1 | 8/2006 | Dorian et al. |
| 2006/0175244 A1 | 8/2006 | Dorian et al. |
| 2006/0178610 A1 | 8/2006 | Nowakowski |
| 2006/0196885 A1 | 9/2006 | Leach et al. |
| 2006/0243676 A1 | 11/2006 | Swift et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0034579 A1 | 2/2007 | Dorian et al. |
| 2007/0036768 A1 | 2/2007 | Fraser et al. |
| 2007/0075016 A1 | 4/2007 | Leach |
| 2007/0208321 A1 | 9/2007 | Leach et al. |
| 2008/0011684 A1 | 1/2008 | Dorian et al. |
| 2008/0164204 A1 | 7/2008 | Hatamian et al. |
| 2008/0173593 A1 | 7/2008 | Coull et al. |
| 2008/0193424 A1 | 8/2008 | McKale et al. |
| 2008/0210645 A1 | 9/2008 | Coull et al. |
| 2008/0217263 A1 | 9/2008 | Higgins et al. |
| 2008/0217264 A1 | 9/2008 | Leach et al. |
| 2008/0217265 A1 | 9/2008 | Leach et al. |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0306431 A1 | 12/2008 | Yoo |
| 2008/0318317 A1 | 12/2008 | Roche et al. |
| 2009/0014391 A1 | 1/2009 | Leach et al. |
| 2009/0018313 A1 | 1/2009 | Shanbrom |
| 2009/0101599 A1 | 4/2009 | Dorian et al. |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0289014 A1 | 11/2009 | Hoeppner |
| 2010/0055087 A1 | 3/2010 | Higgins et al. |
| 2010/0140182 A1 | 6/2010 | Chapman et al. |
| 2010/0186676 A1 | 7/2010 | Van Der Berg |
| 2010/0206798 A1 | 8/2010 | Dorian et al. |
| 2010/0256595 A1 | 10/2010 | Leach et al. |
| 2010/0323870 A1 | 12/2010 | Leach et al. |
| 2010/0324450 A1 | 12/2010 | Leach et al. |
| 2011/0014705 A1 | 1/2011 | Leach et al. |
| 2011/0020196 A1 | 1/2011 | Grippi et al. |
| 2011/0021334 A1 | 1/2011 | Leach et al. |
| 2011/0036786 A1 | 2/2011 | Ellsworth |
| 2011/0056893 A1 | 3/2011 | Leach et al. |
| 2011/0065183 A1 | 3/2011 | Dorian et al. |
| 2011/0077596 A1 | 3/2011 | Higgins et al. |
| 2011/0168193 A1 | 7/2011 | Leach et al. |
| 2011/0192804 A1 | 8/2011 | Landrigan et al. |
| 2011/0251041 A1 | 10/2011 | Chavarria et al. |
| 2012/0015796 A1 | 1/2012 | Leach et al. |
| 2014/0051061 A1 | 2/2014 | Landrigan et al. |
| 2014/0091048 A1 | 4/2014 | Leach et al. |
| 2014/0275497 A1 | 9/2014 | Leach et al. |
| 2014/0349388 A1 | 11/2014 | Dorian et al. |
| 2014/0356446 A1 | 12/2014 | Leach et al. |

FOREIGN PATENT DOCUMENTS

| | | | |
|---|---|---|---|
| CA | 1321138 | 8/1993 | |
| CA | 2182862 | 6/1996 | |
| CA | 2448415 A1 | 12/2002 | |
| CN | 1074709 | 7/1993 | |
| CN | 1321103 A | 11/2001 | |
| CN | 1322146 A | 11/2001 | |
| CN | 103702729 A | 4/2014 | |
| DE | 56103 | 10/1860 | |
| DE | 1443359 | 11/1968 | |
| DE | 4132480 A1 * | 4/1993 | ............. B01L 3/502 |
| DE | 4202667 | 5/1993 | |
| EP | 090997 | 10/1983 | |
| EP | 0102773 | 3/1984 | |
| EP | 0109374 | 5/1984 | |
| EP | 0142339 | 5/1985 | |
| EP | 0244834 A2 | 11/1987 | |
| EP | 0253198 | 1/1988 | |
| EP | 0295771 | 12/1988 | |
| EP | 0417818 | 3/1991 | |
| EP | 534178 | 3/1993 | |
| EP | 0534178 | 3/1993 | |
| EP | 0592242 | 4/1994 | |
| EP | 1005910 | 6/2000 | |
| EP | 1006360 A2 | 6/2000 | |
| EP | 1289618 | 3/2003 | |
| EP | 1406492 B1 | 4/2004 | |
| EP | 1427279 A1 | 6/2004 | |
| EP | 1467746 A2 | 10/2004 | |
| EP | 1509326 | 3/2005 | |
| EP | 1670315 A2 | 6/2006 | |
| EP | 1716901 | 11/2006 | |
| EP | 2887977 A1 | 7/2015 | |
| GB | 854715 | 11/1960 | |
| JP | 60-053845 | 3/1985 | |
| JP | 60250014 A | 12/1985 | |
| JP | 2036872 | 2/1990 | |
| JP | 02071747 | 3/1990 | |
| JP | 2000-189407 A | 7/2000 | |
| JP | 2000199760 A | 7/2000 | |
| JP | 02129224 | 10/2000 | |
| JP | 2004-305439 A | 11/2004 | |
| JP | 2005013783 A | 1/2005 | |
| JP | 200598704 | 4/2005 | |
| JP | 2005524451 | 8/2005 | |
| JP | 2006-305365 A | 11/2006 | |
| JP | 2006527025 A | 11/2006 | |
| JP | 2008104789 A | 5/2008 | |
| JP | 2009-155234 A | 7/2009 | |
| WO | WO-8400905 | 3/1984 | |
| WO | WO-8802259 | 4/1988 | |
| WO | WO-9010031 | 9/1990 | |
| WO | WO-9222312 | 12/1992 | |
| WO | WO-9305067 | 3/1993 | |
| WO | WO-9308904 | 5/1993 | |

(56) References Cited

FOREIGN PATENT DOCUMENTS

| WO | WO-9407548 | | 4/1994 |
| --- | --- | --- | --- |
| WO | WO-9617871 | | 6/1996 |
| WO | WO-9617871 | A1 | 6/1996 |
| WO | WO-9848938 | A1 | 11/1998 |
| WO | WO-0061256 | | 10/2000 |
| WO | WO-0074713 | A1 | 12/2000 |
| WO | WO-0103756 | | 1/2001 |
| WO | WO-0183068 | | 11/2001 |
| WO | WO-0238610 | A1 | 5/2002 |
| WO | WO-02060925 | A1 | 8/2002 |
| WO | WO-02098566 | A2 | 12/2002 |
| WO | WO-03015800 | | 2/2003 |
| WO | WO-03024215 | A1 | 3/2003 |
| WO | WO-03/053362 | A2 | 7/2003 |
| WO | WO-03/088905 | | 10/2003 |
| WO | WO-03/092894 | | 11/2003 |
| WO | WO-03/099412 | A1 | 12/2003 |
| WO | WO-2004009207 | | 1/2004 |
| WO | WO-2004104553 | | 12/2004 |
| WO | WO-2005/034843 | A2 | 4/2005 |
| WO | WO-2006041406 | A1 | 4/2006 |
| WO | WO-2007127834 | A2 | 11/2007 |
| WO | WO-2007142908 | A1 | 12/2007 |
| WO | WO-2008127639 | A1 | 10/2008 |
| WO | WO-2009021257 | A1 | 2/2009 |
| WO | WO-2009111338 | A1 | 9/2009 |
| WO | WO-2011008836 | A1 | 1/2011 |
| WO | WO-2014035964 | A1 | 3/2014 |

OTHER PUBLICATIONS

English language machine translation of DE 4132480 A1.*
International Preliminary Report on Patentability and Written Opinion mailed on Mar. 12, 2015 for PCT/US2013/056793 claiming benefit of U.S. Appl. No. 13/595,461, filed Aug. 27, 2012.
Preliminary Notice of Reasons for Rejection for Japanese Patent Application No. 2014-024420 mailed on Feb. 24, 2015.
Japanese Office Action mailed Sep. 9, 2014 for Japan Patent Application No. 2012-520742,which claims benefit of PCT/US2010/041942 filed Jul. 14, 2010, which claims benefit of U.S. Appl. No. 12/504,413, filed Jul. 16, 2009.
Chinese Office Action mailed Jun. 30, 2014 for Chinese Patent Application No. 201080019707.7, which claims benefit of PCT/US2010/029957 filed Apr. 5, 2010, which claims benefit of U.S. Appl. No. 12/417,789, filed Apr. 3, 2009.
Minivalve international: duckbill valves—du 054.001 sd, <http://www.minivalve.com/htm/DV054.htm>, Accessed Jun. 30, 2014, 1 page.
Momentive Silopren*LSR 2050, Jun. 30, 2014, 3 pages.
Vernay Product Information Sheet, Umbrella Check Valve, Part No. V251010200, Jul. 2013, 2 pages.
"Cell Isolation Techniques, Methods and Materials, Working with Enzymes," (2004) (9 pages) Worthington Biochemical Corp.
"Cell Isolation Theory, Tissue Types," (2004) (5 pages) Worthington Biochemical Corp.
"Centrifuge Tubes" Corning Costar brochure. 1996/1997 Catalog pp. 76-77.
"Frequently Asked Questions, 1. Kits, 2. Enzymes," (2003) 3 pages Worthington Biochemical Corp.
"Trypsinization of Adherent Cells," (undated) 2 pages.
Anesthesiology, vol. 81, No. 4, pp. 1074-1077, Oct. 1994, Hiromasa Mitsuhata, M.D., et al., "An Anaphylactic Reaction to Topical Fibrin Glue".
Ann Thorac Surg, vol. 53, pp. 530-531, 1992, Mehmet C. Oz, M.D., et al., "Autologous Fibrin Glue From Intraoperatively Collected Platelet-Rich Plasma".
Ann Thorac Surg, vol. 56, pp. 387-389, 1993, Robert L. Quigley, M.D., et al., "Intraoperative Procurement of Autologous Fibrin Glue".

Badiavas, et al., "Treatment of Chronic Wounds With Bone Marrow-Derived Cells," (Reprinted) Arch Dermatol. 139:510-516 (Apr. 2003).
Bang, N.U., et al., "Plasma Protein Requirements for Human Platelet Aggregation" Ann. N.Y. Acad Sci, 201:280-299 (1972).
Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31:3 (1991): 408-11.
Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," *J Thorac Cardiovasc Surg* 105:5 (1993): 892-7.
BioCUE™ Platelet Concentration System, Jun. 2010. (2 pages).
Biopolymers, vol. 27, pp. 763-774, 1988, Gerald Marx, "Mechanism of Fibrin Coagulation Based on Selective, Cation-Driven, Protofibral Association".
Boomgaard, et al., "Pooled Platelet Concentrates Prepared by the Platelet-Rich-Plasma Method and Filtered with Three Different Filters and Stored for 8 Days." Vox Sanq, vol. 68: 82-89, Feb. 1995.
Brodke, et al., "Bone Grafts Prepared with Selective Cell Retention Technology Heal Canine Segmental Defects as Effectively as Autograft", SCR-Enriched Bone Grafts Heal Canine Segmental Defects, Journal of Orthopaedic Research (May 2006) pp. 857-866.
Casali, B., F. Rodeghiero, A. Tosetto, B. Palmieri, R. Immovilli, C. Ghedini, and P. Rivasi. "Fibrin glue from single-donation autologous plasmapheresis." Transfusion 32:7 (1992): 641-3.
Clayden J D et al: "Improved segmentation reproducibility in group tractography using a quantitative tract similarity measure" Neuroimage, Academic Press, Orlando, FL, US LNKD-DOI: 10.1016/J.Neuroimage. 2006.07.016, vol. 33, No. 2, Nov. 1, 2006 (Nov. 1, 2006), pp. 482-492.
CLOTALYST™ Automatic Clotting Factor, Would you like to have an autologous thrombin for rapid clotting and haemostasis?, brochure, Biomet Biologics, Inc., Feb. 2007 (12 pages).
Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 (May 1976).
Connolly, "Injectable Bone Marrow Preparations to Stimulate Osteogenic Repair," Clinical Orthopaedics and Related Research 313:8-18 (Apr. 1995).
Connolly, John, M.D., et al. "Development of an Osteogenic Bone-Marrow Preparation." The Journal of Bone and Joint Surgery, Incorporated. vol. 71-A, No. 5 (Jun. 1989) pp. 684-691.
Dallari, et al., "In Vivo Study on the Healing of Bone Defects Treated with Bone Marrow Stromal Cells, Platelet-Rich Plasma, and Freeze-Dried Bone Allografts, Alone and in Combination," Healing of Bone Defects, Journal of Orthopaedic Research (May 2006) pp. 877-888.
De Ugarte, et al., "Comparison of Multi-Lineage Cells from Human Adipose Tissue and Bone Marrow," Cells Tissues Organs 174:101-109 (2003).
De Ugarte, et al., "Differential Expression of Stem Cell Mobilization-Associated Molecules on Multi-Lineage Cells from Adipose Tissue and Bone Marrow," Immunology Letters 89:267-270 (2003).
De Wit, et al. "Experiments on the Preparation of Blood Components with the IBM 2991 Blood Cell Processor" Vox Sang. 29: 352-362 (Feb. 10, 1975).
DelRossi, A. J., A. C. Cernaianu, R. A.Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100:2 (Aug. 1990): 281-6.
DePalma, L., et al., "The preparation of fibrinogen concentrate for use as fibrin glue by four different methods." Transfusion (1993) vol. 33, No. 9; pp. 717-720.
DeUgarte, M.D., Daniel A., et al., "Future of Fat as Raw Material for Tissue Regeneration," (Feb. 2003) pp. 215-219, Lippincott Williams & Wilkins, Inc.

(56) References Cited

OTHER PUBLICATIONS

DiMuzio, Paul et al., "Development of a Tissue-Engineered Bypass Graft Seeded with Stem Cells," Vasucular, vol. 14, No. 6, (2006) pp. 338-342, BC Decker, Inc.
Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".
Edlich, Richard F., George T. Rodeheaver, and John G. Thacker. "Surgical Devices in Wound Healing Management." In *Wound Healing: Biochemical & Clinical Aspects*,ed. I. Kelman Cohen, Robert F. Diegelmann, and William J. Lindblad. 581-600. 1st ed., vol. Philadelphia: W.B. Saunders Company, 1992.
Ehricke H H et al: "Visualizing MR diffusion tensor fields by dynamic fiber tracking and uncertainty mapping" Computers and Graphics, Elsevvier, GB LNKD-DOI: 10.1016/J. CAG.2006.01. 031, vol. 30, No. 2, Apr. 1, 2006 (Apr. 1, 2006), pp. 255-264.
Eppley, et al., "Platelet Quantification and Growth Factor Analysis from Platelet-Rich Plasma: Implications for Wound Healing," Plastic and Reconstructive Surgery, 114(6):1502-1508 (Nov. 2004).
Epstein, G. H., R. A. Weisman, S. Zwillenberg, and A. D. Schreiber. "A new autologous fibrinogen-based adhesive for otologic surgery." *Ann Otol Rhinol Laryngol* 95 (May 25-26, 1985) 40-5.
European Communication Pursuant to Article 94(3) EPC mailed May 6, 2013 for PCT/US2010/029957 which claims benefit of U.S. Appl. No. 12/417,789, filed Apr. 3, 2009.
First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (Aug. 15, 1975): 495-501.
Floryan, K. et al. "Home Study Program: Intraoperative Use of Autologous Platelet-Rich and Platelet-Poor Plasma for Orthopedic Surgery Patients" vol. 80, No. 4 (Oct. 2004) p. 667-674.
Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.
Friesen, M.D., Robert, et al. "Blood Conservation During Pediatric Cardiac Surgery: Ultrafiltration of the Extracorporeal Circuit Volume After Cardiopulmonary Bypass." Anesth. Analg 1993: 77-702-7.
Galois, et al., "Cartilage Tissue Engineering: State-of-the-Art and Future Approaches," Pathol Biol (Paris), 53(10), Dec. 2005.
Gibble, J. W. and P. M. Ness. "Fibrin glue: the perfect operative sealant?" *Transfusion* 30 (1990): 741-7.
Gimble, Jeffrey M., "Adipose-Derived Stem Cells for Regenerative Medicine," Circulation Research (May 11, 2007) pp. 1249-1260, American Heart Association, Inc.
Gomillion, Cheryl T., et al., "Stem cells and adipose tissue engineering," Biomaterials 27, Science Direct (2006) pp. 6052-6063, Elsevier.
GPS® III System, GPS® III Platelet Separation System, Leadership through Technology, brochure, Jul. 2007 (8 sheets).
GPS® System, "GPS® Platelet Concentrate System," Cell Factor Technologies, Inc., Biomet Orthopaedics, Inc., (Feb. 29, 2004) (9 pages).
GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.
GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.
GPS® II System, Gravitational Platelet Separation System, "Accelerating the Body's Natural Healing Process," Biomet Biologics (Jul. 15, 2006) 16 pages.
GPS® II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.
GPS® II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.
Guilak, Frank, et al., "Adipose-derived adult stem cells for cartilage tissue engineering," Biorheology 41 (2004) pp. 389-399, IOS Press.
Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.
Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (Mar. 1992): 357-9.
Hattori, et al., "Osteogenic Potential of Human Adipose Tissue-Derived Stromal Cells as an Alternative Stem Cell Source," Cells Tissues Organs (2004) 178:2-12 Karger.
Haynesworth, S.E. et al. "Mitogenic Stimulation of Human Mesenchymal Stem Cells by Platelet Releasate Suggests a Mechanism for Enhancement of Bone Repair by Platelet Concentrate" 48th Annual Meeting of the Orthopaedic Research Society Poster No. 0462 (2002).
Hennis, H. L., W. C. Stewart, and E. K. Jeter. "Infectious disease risks of fibrin glue [letter]." *Ophthalmic Surg* 23 (Sep. 1992): 640.
Hernigou, et al., "Percutaneous Autologous Bone-Marrow Grafting for Nonunions. Influence of the Number and Concentration of Progenitor Cells," Journal of Bone & Joint Surgery, 87A(7):1430-1437 (Jul. 2005).
Hom, D., et al. "Promoting Healing with Recombinant Human Platelet-Derived Growth Factor-BB in a Previously Irradiated Problem Wound." The Laryngoscope, vol. 113 (pp. 1566-1671) Sep. 2003.
Hood, Andrew G., et al., "Perioperative Autologous Sequestration III: A New Physiologic Glue with Wound Healing Properties," (Jan. 1993) vol. 14 pp. 126-129.
International Preliminary Examination Report and Written Opinion issued Aug. 31, 2010 for PCT/US2009/035564 claiming benefit of U.S. Appl. No. 61/078,178, filed Jul. 3, 2008, which priority is also claimed of said provisional case by U.S. Appl. No. 12/395,085, filed Feb. 27, 2009.
International Preliminary Report on Patentability and Written Opinion mailed Oct. 13, 2011 for PCT/US2010/029957 which claims benefit of U.S. Appl. No. 12/417,789, filed Apr. 3, 2009.
International Preliminary Report on Patentability and Written Opinion mailed Oct. 31, 2013 for PCT/US2012/034104 claiming benefit of U.S. Appl. No. 13/089,591, filed Apr. 19, 2011.
International Preliminary Report on Patentability completed Aug. 13, 2009 for PCT/US2008/004687 claiming benefit of U.S. Appl. No. 60/911,407, filed Apr. 12, 2007.
International Preliminary Report on Patentability mailed Jan. 26, 2012 for PCT/US2010/041942 claiming benefit of U.S. Appl. No. 12/504,413, filed Jul. 16, 2009.
International Search Report and Written Opinion mailed Aug. 9, 2011 for PCT/US2011/031954 claiming benefit of U.S. Appl. No. 12/758,127, filed Apr. 12, 2010.
International Search Report and Written Opinion mailed Dec. 5, 2013 for PCT/US2013/056793 claiming benefit of U.S. Appl. No. 13/595,461, filed Aug. 27, 2012.
International Search Report and Written Opinion mailed Jul. 2, 2008 for International Application No. PCT/US2008/004687 which claims priority to U.S. Appl. No. 60/911,407, filed Apr. 12, 2007.
International Search Report and Written Opinion mailed Jul. 3, 2009 for PCT/US2009/035564 claiming benefit of U.S. Appl. No. 61/078,178, filed Jul. 3, 2008.
International Search Report and Written Opinion mailed Jul. 30, 2010 for PCT/US2010/029957 which claims benefit of U.S. Appl. No. 12/417,789, filed Apr. 3, 2009.
International Search Report and Written Opinion mailed Nov. 7, 2011 for PCT/US2011/045290 claiming benefit of U.S. Appl. No. 12/846,944, filed Jul. 30, 2010.
International Search Report and Written Opinion mailed Oct. 8, 2010 for PCT/US2010/041942 claiming benefit of U.S. Appl. No. 12/504,413, filed Jul. 16, 2009.

(56) References Cited

OTHER PUBLICATIONS

International Search Report for International Application No. PCT/US/0316506 mailed Oct. 13, 2003 which claims benefit of U.S. Appl. No. 60/383,013, filed May 24, 2002.
International Search Report for International Application No. PCT/US2007/012587 mailed Nov. 6, 2007 which claims benefit of U.S. Appl. No. 11/441,276, filed May 25, 2006.
International Search Report for PCT/US2012/034104 mailed Oct. 29, 2012, claiming benefit of U.S. Appl. No. 13/089,591, filed Apr. 18, 2012.
Invitation to Pay Additional Fees and, Where Applicable, Protest Fee mailed Aug. 6, 2012 for PCT/US2012/034104 claiming benefit of U.S. Appl. No. 13/089,591, filed Apr. 19, 2011.
Ishida, et al., "Platelet-Rich Plasma With Biodegradable Gelatin Hydrogel Promotes Rabbit Meniscal Tissue Regeneration," 52nd Annual Meeting of the Orthopaedic Research Society Paper No. 1035, 1 page (2006).
Jackson, C. M. and Y. Nemerson. "Blood coagulation." *Annu Rev Biochem* 49 (1980): 765-811).
Japan Office Action mailed Aug. 23, 2013 for Japan Patent Application No. 2010-503066.
Japan Office Action mailed Jan. 22, 2013 for Japan Application No. 2010-503066.
Japanese Office Action mailed May 20, 2014 for Japanese Application No. JP2012-503768.
Jayadev, Suprya. "Trypsinization of Adherent Cells." Aug. 8, 1991. Web. Apr. 14, 2010 http://www.duke.edu/web/ceramide/protocols/0005.html.
Johnstone, et al., "Autologous Mesenchymal Progenitor Cells in Articular Cartilage Repair", Clinical Orthopaedics and Related Research 367S:S156-S162 (Oct. 1999).
Jones D K et al: "Confidence mapping in diffusion ensor magnetic resonance imaging tractography using a bootstrap approach" Magnetic Resonance in Medicine Wiley USA, vol. 53 , No. 5, May 2005 (May 2005), pp. 1143-1149.
Journal of Oral Maxillofacial Surgery, vol. 43, pp. 605-611, Helene Matras, M.D., "Fibrin Seal: The State of the Art" (1985).
Karpatkin, S., "Heterogeneity of Human Platelets. VI., Correlation of Platelet Function with Platelet Volume", Blood, vol. 51, No. 2 (Feb. 1978).
Kjaergard, H. K,, U. S. Weis-Fogh, H. Sorensen, J. Thiis, and I. Rygg. "A simple method of preparation of autologous fibrin glue by means of ethanol." *Surg Gynecol Obstet* 175 (1992): 72-3.
Kjaergard, H. K., Fogh Us Weis, and J. J. Thiis. "Preparation of autologous fibrin glue from pericardial blood." *Ann Thorac Sur* 55 (1993): 543-4.
Kumar, Vijay et al. "Stability of Human Thrombin Produced From 11 ml of Plasma Using the Thrombin Processing Device," Journal of American Society of Extra-Corporeal Technology. JECT: Mar. 2005:37; 390-395.
Kumar, Vijay et al. "Whole Blood Thrombin: Development of a Process for Intra-Operative Production of Human Thrombin." Journal of American Society of Extra-Corporeal Technology. JECT: Apr. 2007; 39:18-23.
Kumar, Vijay et al., "Autologous Thrombin: Intraoperative Production From Whole Blood." Journal of American Society of Extra-Corporeal Technology. JECT: Apr. 2008; 40:94-98.
Laryngoscope vol. 99, pp. 974-976, Sep. 1989, Kyosti Laitakari, M.D., et al., "Autologous and Homologous Fibrinogen Sealants: Adhesive Strength".
Laryngoscope, vol. 95, pp. 1074-1076, Sep. 1985, Karl H. Siedentop, M.D., et al., "Autologous Fibrin Tissue Adhesive".
Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".
Lerner, R. and N. S. Binur. "Current status of surgical adhesives." *J Surg Res* 48 (Feb. 1990): 165-81.
Longas, Maria O., "An Improved Method for the Purification of Human Fibrinogen." J. Biochem (1980) vol. 11, pp. 559-564.

Lori N F et al: "Diffusion tensor fiber tracking of human brain connectivity: acquisition methods, reliability analysis and biological results" NMR in Biomedicine Wiley UK, vol. 15, No. 7-8, Nov. 2002 (Nov. 2002), pp. 493-515.
Lu, et al., "Bone Marrow Mesenchymal Stem Cells: Progress in Bone/Cartilage Defect Repair," 19(1), Jan. 2002.
Marrowstim Concentration System, Biomet Biologics, Inc., 20 pages (REV Feb. 15, 2008).
Marx, Gerard, et al., "Heat Denaturation of Fibrinogen to Develop a Biomedical Matrix." Journal of Biomedical Materials Research Part B: Applied Biomaterials (Apr. 2007) pp. 49-57.
Masri, Marwan A., et al. "Isolation of Human Fibrinogen of High Purity and in High Yield Using Polyethylene Glycol 1000." Thromb Haemostas (Struttgart) (1983) vol. 49 (2); pp. 116-119.
Matras, Helene, H. P. Dinges, H. Lassmann, and B. Mamoli. "Zur nahtlosen interfaszikularen Nerventransplantation im Tierexperiment." Wein Med Woschtr 122:37 (1972): 517-523.
Minntech® Filtration Technologies Group, "Hemocor HPH® Hemoconcentrator," Minntech Corporation (2004); http://www.minntech.com/ftg/products/hph/index.html, printed Jul. 15, 2004 (2 pages).
Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).
Minntech® Filtration Technologies Group, "Renaflo® II Hemofilter," Minntech Corporation (2004); http://www.minntech.com/ftg/products/renaflo/index.html, printed Jul. 15, 2004 (2 pages).
Molnar, Amy, "Stem Cells from Muscles Can Repair Cartilage, Study Finds Genetically Engineered Muscle-Derived Stem Cells Improved Cartilage Repair in Rats", American College of Rheumatology, (2005).
Moretz, W., Jr., J Shea Jr., J. R. Emmett, and J Shea. "A simple autologous fibrinogen glue for otologic surgery." *Otolaryngol Head Neck Surg* 95 (Jul. 1986): 122-4.
Nakagami, Hironori, et al., "Novel Autologous Cell Therapy in Ischemic Limb Disease Through Growth Factor Secretion by Cultured Adipose Tissue-Derived Stromal Cells," Angiogenesis by Adipose Tissue-Derived Cells, (Dec. 2005) pp. 2542-2547, American Heart Association, Inc.
Nathan, Suresh,, et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.
Nilsson, et al., "Bone Repair Induced by Bone Morphogenetic Protein in Ulnar Defects in Dogs," The Journal of Bone and Joint Surgery, vol. 68 B., No. 4, Aug. 1986.
Notice of Allowance mailed Mar. 24, 2011 for U.S. Appl. No. 12/101,586.
Notice of Allowance mailed May 27, 2010 for U.S. Appl. No. 12/101,594, filed Apr. 11, 2008.
Notice of Allowance mailed Oct. 18, 2011 for U.S. Appl. No. 12/897,401.
Office Action (Final) mailed Mar. 18, 2010 for U.S. Appl. No. 12/101,594, filed Apr. 11, 2008.
Office Action mailed Feb. 3, 2011 for U.S. Appl. No. 12/101,586, filed Apr. 14, 2008.
Office Action mailed Nov. 16, 2010 for U.S. Appl. No. 12/897,401 claiming benefit of U.S. Appl. No. 12/101,594, filed Apr. 11, 2008.
Office Action mailed Oct. 16, 2009 for U.S. Appl. No. 12/101,594, filed Apr. 11, 2008.
Office Action mailed Sep. 20, 2010 for U.S. Appl. No. 12/101,586, filed Apr. 14, 2008.
Orphardt, Charles E., "Denaturation of Proteins," Virtual Chembook, Elmhurst College (2003) 3 pages. http://www.elmhurst.edu/~chm/vchembook/568denaturation.html (web accessed Mar. 9, 2011).
Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".

(56) References Cited

OTHER PUBLICATIONS

Parchment et al., Roles for in vitro myelotoxicity tests in preclincial drug development and clinical trial planning, Toxicology Pathology, Society of Toxicological Pathologists, vol. 21, No. 2, 1993, pp. 241-250.
Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.
Planat-Bénard, V., et al., "Spontaneous Cardiomyocyte Differentiation From Adipose Tissue Stroma Cells," Adipose-Derived Cell Cardiomyocyte (Feb. 6, 2004) pp. 223-229 American Heart Association, Inc.
Ponticiello, Michael S., "A Rapid Technique for the Isolation and Concentration of Stem Cells from Human Bone Marrow", Cell Factor Technologies, Inc. (2006) 2 pages.
Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.
Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Apr. 15, 2007) pp. 1409-1422.
Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (Apr. 15, 2007) pp. 1423-1424.
Sanal, M. "Does fibrin glue cause foreign body reactions? [letter]." *Eur J Pediatr Surg* 3 (1992): 190 (1 page).
Sanal, M., H. Dogruyol, A. Gurpinar, and O. Yerci. "Does fibrin glue cause foreign body reactions?" *Eu r J Pediatr Surg* 2 (1992): 285-6.
Schmidt, K.G., et al., "Labelling of Human and Rabbit Platelets with Indium-Oxine Complex", 23:97-106 (1979).
Schmidt, K.G., et al., "Preparation of Platelet Suspensions from Whole Blood in Buffer", Scand. J. Hoemato, 23:88-96 (1979).
Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (Apr. 10, 2007) pp. 818-827 AlphaMed Press.
Semple, Elizabeth, PhD, et al. "Quality of Thrombin Produced From the Patient's Own Plasma Using the TPD™, a New Thrombin-Processing Device." Journal of American Society of Extra-Corporeal Technology. JECT: 2005; 37:196-200.
Sierra, D. H. "Fibrin sealant adhesive systems: a review of their chemistry, material properties and clinical applications." *J Biomater Appl* 7 (Apr. 1993): 309-52.
Sigma-Aldrich® Alkaline Phosphatase (Procedure No. 85), drug fact sheet, (2003) pp. 1-2, Sigma-Aldrich, Inc.
Silver, Frederick H., et al., "Review Preparation and use of fibrin glue in surgery." Biomaterials 16 (1995) pp. 891-903.
Solem, Jan Otto, et al., "Hemoconcentration by Ultrafiltration During Open-Heart Surgery," Scand J Thor Cardiovasc Surg 22:271-274, 1988.
Sutton, Robin G., et al. "Comparison of Three Blood-Processing Techniques During and After Cardiopulmonary Bypass." Ann Thorac Surg (1993) vol. 56; pp. 941-943.
Takahashi, Kazutoshi et al., "Induction of Pluripotent Stem Cells from Adult Human Fibroblasts by Defined Factors," Cell, (Nov. 30, 2007) pp. 1-12, Elsevier Inc.
The American Journal of Surgery, vol. 168, pp. 120-122, Aug. 1994, Roy L. Tawes, Jr., M.D., et al., "Autologous Fibrin Glue: The Last Step in Operative Hemostatis".
The American Surgeon, vol. 55, pp. 166-168, Mar. 1989, William D. Spotnitz, M.D., et al., "Successful Use of Fibrin Glue During 2 Years of Surgery at a University Medical Center".
Weis-Fogh, U. S. "Fibrinogen prepared from small blood samples for autologous use in a tissue adhesive system." Eur Surg Res 20 (1988): 381-9.
Weisman, MD., Robert A., "Biochemical Characterization of Autologous Fibrinogen Adhesive," Laryngoscope 97: Oct. 1987; pp. 1186-1190.
Wiseman, David M., David T. Rovee, and Oscar M. Alverez. "Wound Dressings: Design and Use." In *Wound Healing: Biochemical & Clinical Aspects*, ed. I. Kelman Cohen, Robert F. Diegelmann, and William J. Lindblad. 562-580. 1st ed., vol. Philadelphia: W. B. Saunders Company, 1992.
Woodell-May, et al., "Producing Accurate Platelet Counts for Platelet Rich Plasma: Validation of a Hematology Analyzer and Preparation Techniques for Counting," Scientific Foundation, Journal of Carniofacial Surgery 16(5):749-756 (Sep. 2005).
Written Opinion of the International Preliminary Examining Authority mailed Mar. 17, 2009 for International Application No. PCT/US2008/004687 which claims priority to U.S. Appl. No. 60/911,407, filed Apr. 12, 2007.
Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.
Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.
Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.
Chinese Office Action mailed Nov. 21, 2014 for Chinese Patent Application No. 201280030026.X.
"European Application Serial No. 13762636.2, Office Action mailed Apr. 23, 2015", 2 pgs.

\* cited by examiner

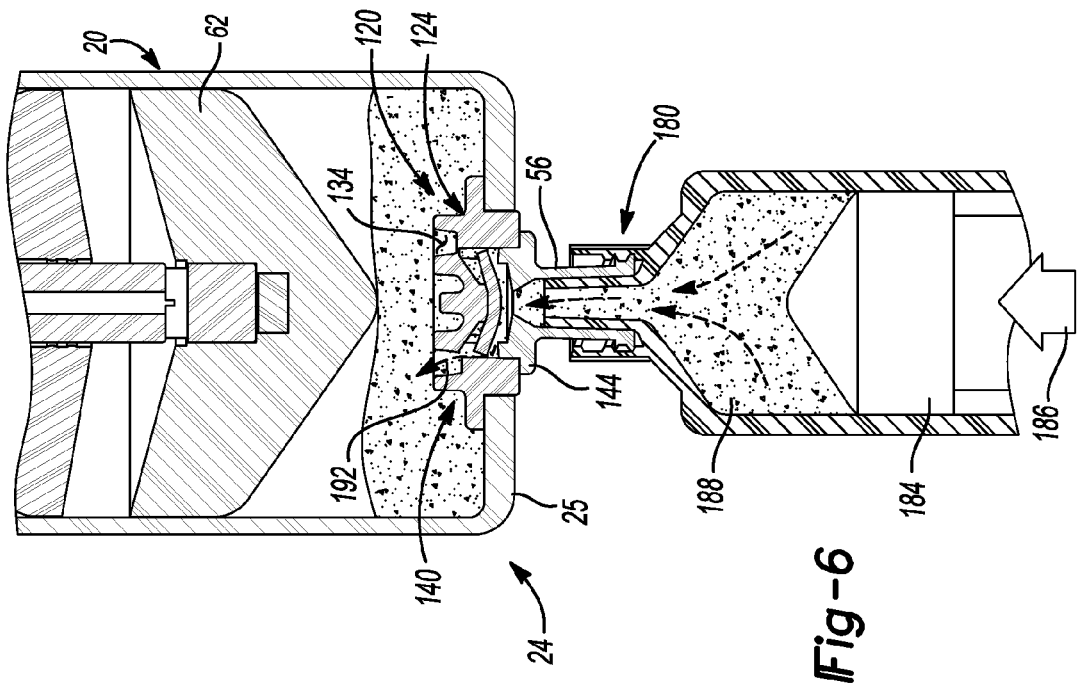
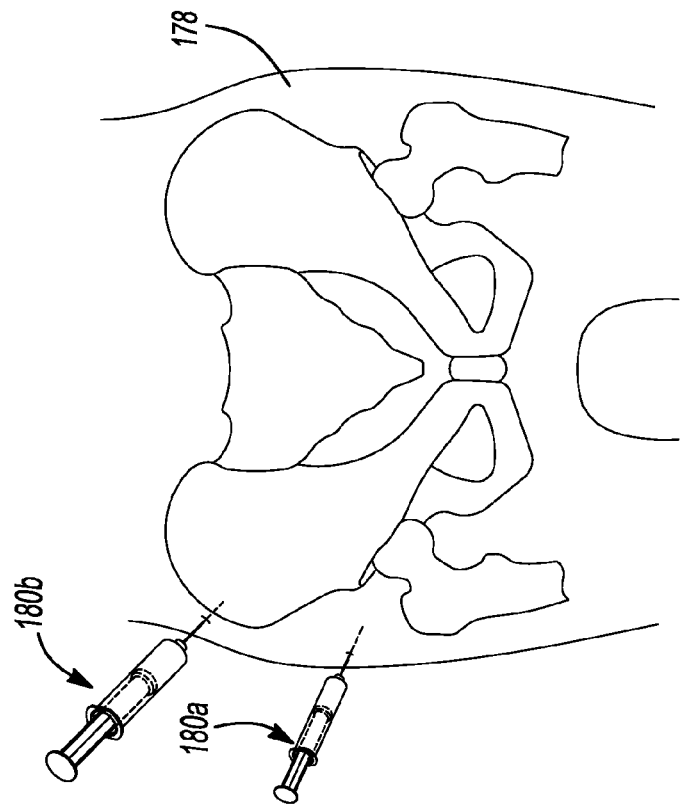

APPARATUS AND METHOD FOR SEPARATING AND CONCENTRATING FLUIDS CONTAINING MULTIPLE COMPONENTS

FIELD

The subject disclosure is related to separating a whole material including multiple components into selected fractions of components, and particularly to a method and apparatus for allowing a float member to operate generally unhindered in a container.

BACKGROUND

This section provides background information related to the present disclosure which is not necessarily prior art.

Clinicians have identified a wide range of therapeutic and laboratory applications for autologous isolated fractions, such as platelet concentrate, platelet-poor-plasma, and stromal cells, of suspensions such as blood, bone marrow aspirate, and adipose tissue. Clinicians generally prefer to draw and fractionate the autologous suspension at the point-of-care. Point-of-care fractionation can reduce the need for multiple appointments to draw and fractionate the autologous suspension which can be costly and inconvenient. Additionally, point-of-care preparation reduces potential degradation of the autologous suspension that can begin once the autologous suspension is removed from a patient. Point-of-care fractionation systems should be easy to operate to reduce the need to provide clinicians with extensive instruction, quick so the therapeutic fraction can be isolated and administered during a single patient visit, efficient to effectively isolate the fraction to a desired concentration, and reproducible to operate over wide variations in suspension characteristics. An example of a buoy based suspension fractionation system is shown in BIOMET BIOLOGICS, Inc. international brochure entitled "*Gravitational Platelet Separation System Accelerating the Body's Natural Healing Process*," 2006.

SUMMARY

This section provides a general summary of the disclosure, and is not a comprehensive disclosure of its full scope or all of its features.

Whole materials can be extracted from various sources, such as a human body or banked materials. For example, whole blood can be withdrawn from a patient or be withdrawn from a blood bank. The whole material, however, can be separated into various components thereof in fractions based upon density and gravity separation. For example, the whole material can be positioned in a separation container and centrifuged to fractionate or separate into fractions the various components in the whole blood. Fractions can include red blood cells, plasma, and a buffy coat including platelets, white blood cells, stromal cells, and various growth factors. The whole material can also include bone marrow, a mixture of blood and bone marrow, adipose, and other materials.

A buoy or float can be positioned within the separation container to assist in a physical separation of the whole material positioned in the separation container. The buoy can be positioned within the container to move between a first end and a second end. The buoy can also provide a physical separation of the first end and the second end. The buoy can include or be formed to have a selected specific gravity or density such that it will move to a selected location within a fractionated whole material so that a portion of the buoy, such as a middle collection area, of the buoy is positioned at a selected location within the fractionated material.

The separation container can include an opening or port into the container for introduction of a whole material which can also be referred to as a multiple component material. The container can include at least one withdrawal port at or near a second end opposite the first end and on a second and opposite side of the buoy for withdrawal of at least a portion of the whole material. A withdrawal tube can also be positioned between at least of one port at the second end of the separation container for connection to the buoy system to allow withdrawal from a middle region or middle collection portion of the buoy. The first portal on the first end of the container can also include a valve, such as a check valve, to limit a direction of flow of material into the separation container.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is an environmental view of a process of withdrawing at least a portion of a whole material from a patient;

FIG. 6 is a partial cross-sectional view of filling the separation container;

Corresponding reference numerals indicate corresponding parts throughout the several views of the drawings.

DETAILED DESCRIPTION

Figure 1:
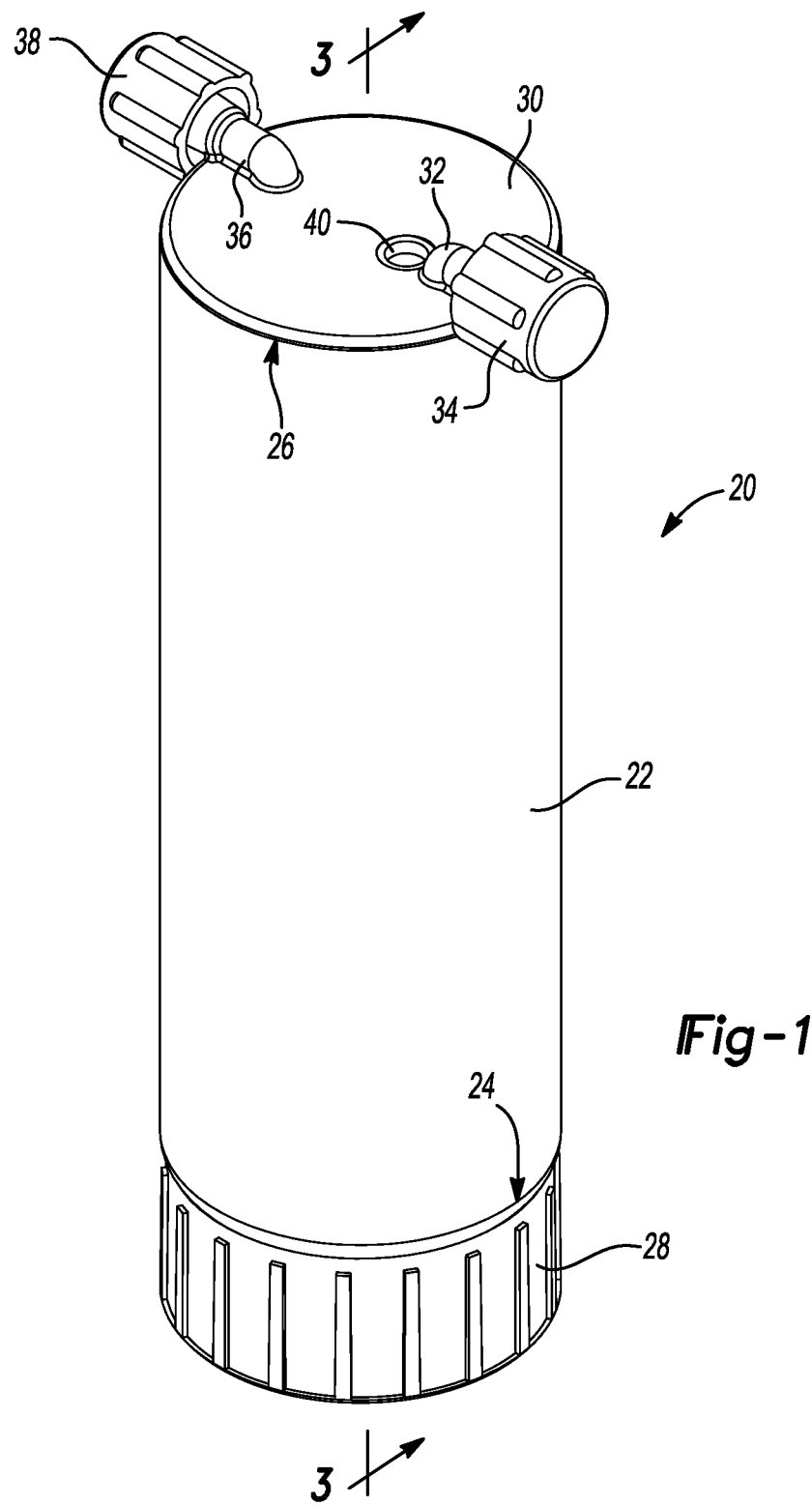
FIG. 1 is an environmental view of a separation container.

Example embodiments will now be described more fully with reference to the accompanying drawings.

A separation container 20 can generally include a sidewall 22 that extends from a first end 24 to a second end 26. The first end 24 can include a first end wall 25 and/or be covered or connected to a stand 28. The stand 28 can assist in maintaining the container 20 in an upright position or vertical position when the container 20 is not positioned in a centrifuge, as discussed further herein. The sidewall 22 extending to the second end 26 can include a second end wall and/or be capped or covered by a cap 30. The cap 30 can be separate and connected to the wall 22 or formed as one piece therewith. Extending through the cap 30 at the second end 26 can be a first port 32 that is covered by a port cap 34 and a second port 36 that is covered by a second port cap 38. In addition, a vent 40 can be formed through the cap 30 that can include a selected filter material such that the interior of the container 20 remains substantially sterile. The vent 40 can be similar to the vent and included filter material in the GPS® II BLOOD SEPARATION DEVICE, sold by BIOMET, Inc., having a place of business in Indiana.

Figure 2:
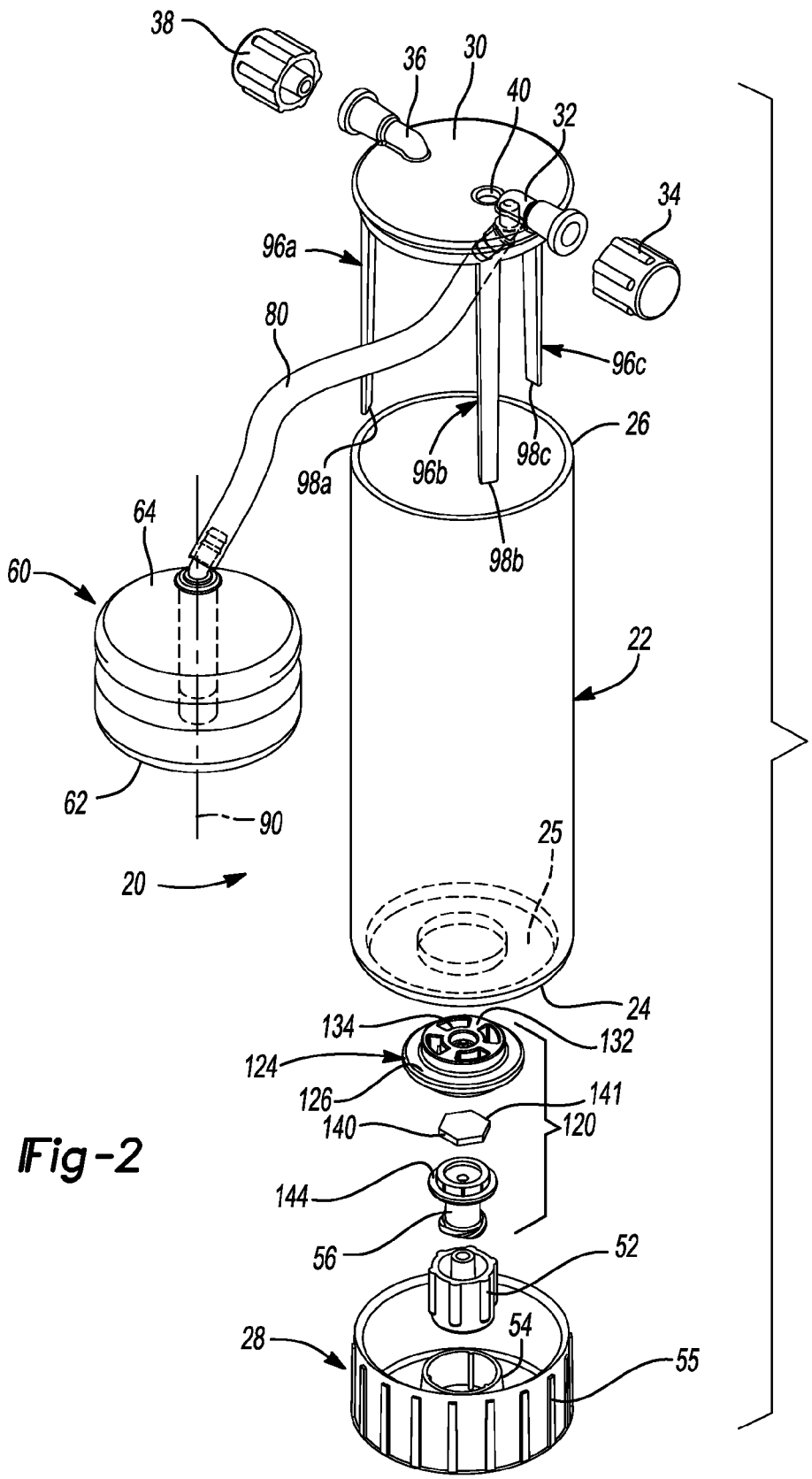
FIG. 2 is an exploded view of the separation container of FIG. 1.
Figure 3:
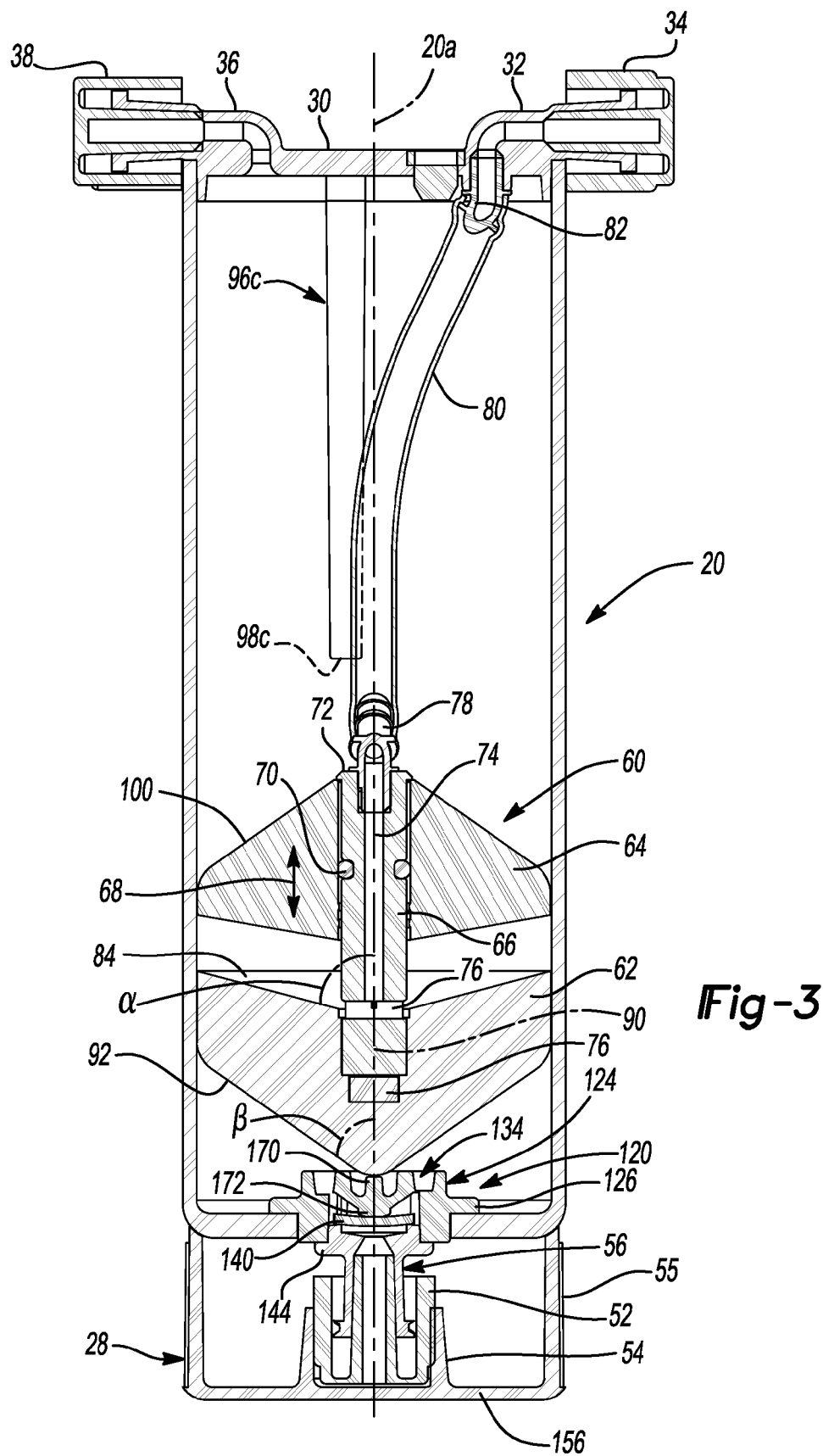
FIG. 3 is a cross-sectional view of the separation container of FIG. 1 along line 3-3.

With continuing reference to FIG. 1 and additional reference to FIGS. 2 and 3, the separation container 20 can be provided by a manufacturer substantially assembled or in multiple pieces, as illustrated in exploded view in FIG. 2. Nevertheless, the stand 28 can be removed or removable to be interconnected with a port, including a luer type port 56 or a cap 52 that interconnects with the luer type connector 56. In particular, the cap 52 can include an exterior wall that can be engaged or coupled to an extending wall or connection portion 54 of the stand 28. An outer extending wall 55 of the stand 28 can be formed to include an outer diameter or dimension that is substantially equivalent to the dimension of the wall 22 of the container 20. The internal area or portion of the stand 28 can therefore be substantially hollow save for the extending or connection portion 54 that engages the cap 52. The interconnection of the stand 28 and the cap 52 can be a friction or interference fit, glued, or can include other connection portions such as a thread or taper. Also, the stand 28 can be formed integrally or one piece, such as to include, the cap 52. In other words, the upstanding wall 54 can include a luer connection to engage the luer type connector 56.

The stand 28 is generally provided to hold the container 20 in a vertical position or upright orientation when placed on a surface. Further, the stand 28 is generally provided to allow the container 20, with the stand 28 in place on the container 20, to be positioned within a bucket of a centrifuge system, and to support the container 20 against centrifugal forces during centrifugation. For example, the stand 28 can contact an edge near the first end 24 to support the container 20 within a centrifuge bucket.

Positionable within the container 20 is a buoy or float system 60. The buoy 60 can include a first buoy member 62 and a second buoy member 64. Interconnecting the first and second buoy members 62, 64 can be a third buoy member or post 66. The third buoy member 66 can allow or have the second buoy member 64 slide along or move along the buoy post 66 generally in the direction of arrow 68. The second buoy member 64 can be sealed relative to the buoy post 66 with an appropriate sealing portion such as a tight fit or an O-Ring 70. A lip or shoulder 72 can limit travel of the second buoy member 64 relative to the first buoy member 62 and the buoy post 66.

Additionally, the buoy post can define a collection passage 74 that includes collection face passages 76. The collection passage 74 can pass through a port or hose connection member 78 to which a hose or tube 80 is connected. The hose 80 can be connected to a second hose connection 82 that can extend from the first port 32. As discussed herein, a member can be interconnected with a first port 32 to allow withdrawal of a material from a collection face or surface 84 of the first buoy member 62 by withdrawing material through the collection passage 74, tube 80, and first port 32. The member can include a tube connection, a syringe, or other appropriate connectable member.

The buoy 60 can be a buoy that is substantially similar to the buoy disclosed in U.S. Pat. No. 8,067,534 or sold in the GPS® II BLOOD SEPARATION DEVICE, sold by BIOMET, Inc. In addition, the buoy system 60 can be similar to the buoy system disclosed in U.S. Pat. No. 7,806,276 presently sold in the GPS® III BLOOD SEPARATION DEVICE, sold by BIOMET, Inc. Accordingly, the buoy system can have a total density of about 1.01 grams per cubic centimeter (g/cm3) to about 1.10 g/cm3. Further, the first buoy member 62 can have a first density different from a second density of the second buoy member 64. Thus, the first buoy member 62 can have the first density of about 1.02 g/cm3 to about 1.10 g/cm3 and the second buoy member 64 can have the second density of about 0.90 g/cm3 to about 1.01 g/cm3. This can assist in allowing the second buoy member 64 to slide along the buoy post 66 during separation of material positioned in the container 20.

The buoy system 60 can generally define a central axis or line 90. It can be selected to assemble the buoy 60 into the container 20 such that the central axis 90 of the buoy 60 is aligned with the longitudinal axis 20a of the container. The collection face 84 can define an angle α relative to the central axis 90 and the buoy bottom or second surface 92 can define an internal angle β relative to the central axis 90. It is understood that a complimentary angle can also be defined from the bottom surface or wall 92 to a line that is substantially normal to the central axis 90. The angle α can be about 55 to about 85 degrees. The angle β can be about 30 to 85 degrees, including about 55 degrees. The angle β can be selected to assist passage of at least a portion of material placed in the container 20 to pass the first buoy member 62. That is, the less the angle β (i.e. the steeper the angle β) the easier for material to pass the first buoy member 62.

Figure 7:
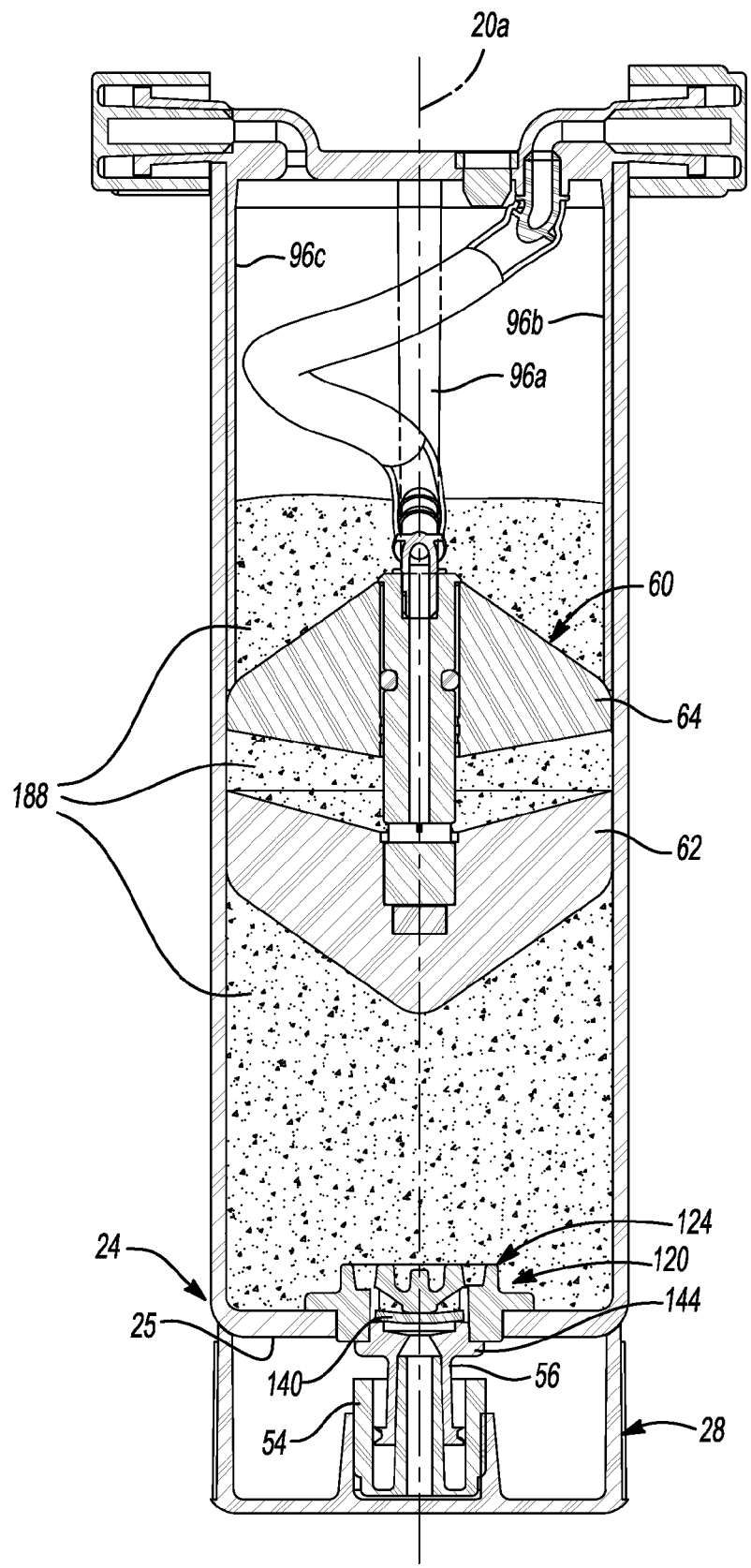
FIG. 7 is a cross-sectional view of the separation container filled with a selected whole material.

The cap 30 can be positioned on the top of the wall 22 to substantially close and/or seal the container 20. Extending from the cap 30 can be stop legs or members 96a-96c. The legs 96a-96c extend from the cap to respective distal ends 98a-c. The distal end of the legs 98a-98c can engage a top surface 100 of the second buoy member 64, as illustrated in FIG. 7, to limit a movement of the buoy member 60 towards the cap 30 during loading and at least partial filling of the container 20 with a fluid, including a biological material 188, a separation, or centrifugation operation of a whole material within the container 20. The limited movement can be predetermined and can be about 30% to about 70%, including about 66% of the total length of the container 20. Thus, the movement of the buoy 60 can be limited within the container 20 when the cap 30 is in place by the legs 96a-96c extending therefrom.

As discussed further herein, the legs 96a-96c can be set at a fixed location relative to one of the ends of the container 20 such that the maximum movement of the buoy system 60 can be maintained within the container 20. It will also be understood, however, that the legs 96a-c can be provided in any appropriate number, such as one leg may be able to provide an appropriate abutment surface area to stop the buoy at a selected location. Additionally, the legs 96a-c can be provided as projections or protuberances from the container 20 that extend into the container 20 that are substantially transverse to a long axis of the container 20.

The container 20, as discussed above, extends from the first end 24 to the second end 26. At the second end 26, the cap 30 can engage the second end or can be formed integrally therewith. At the first end 24, the bottom wall or first end wall 25 can extend from the sidewall 22. The first end wall 25 can further include a valve assembly 120 or at least a portion thereof. The valve assembly 120 allows the container to be filled through the first end 24 while the ports 32, 36 allow the container to be emptied or have material withdrawn from the second end 26. It is understood that the first end 24 may be a bottom end and the second end 26 may be a top end.

Figure 4A:
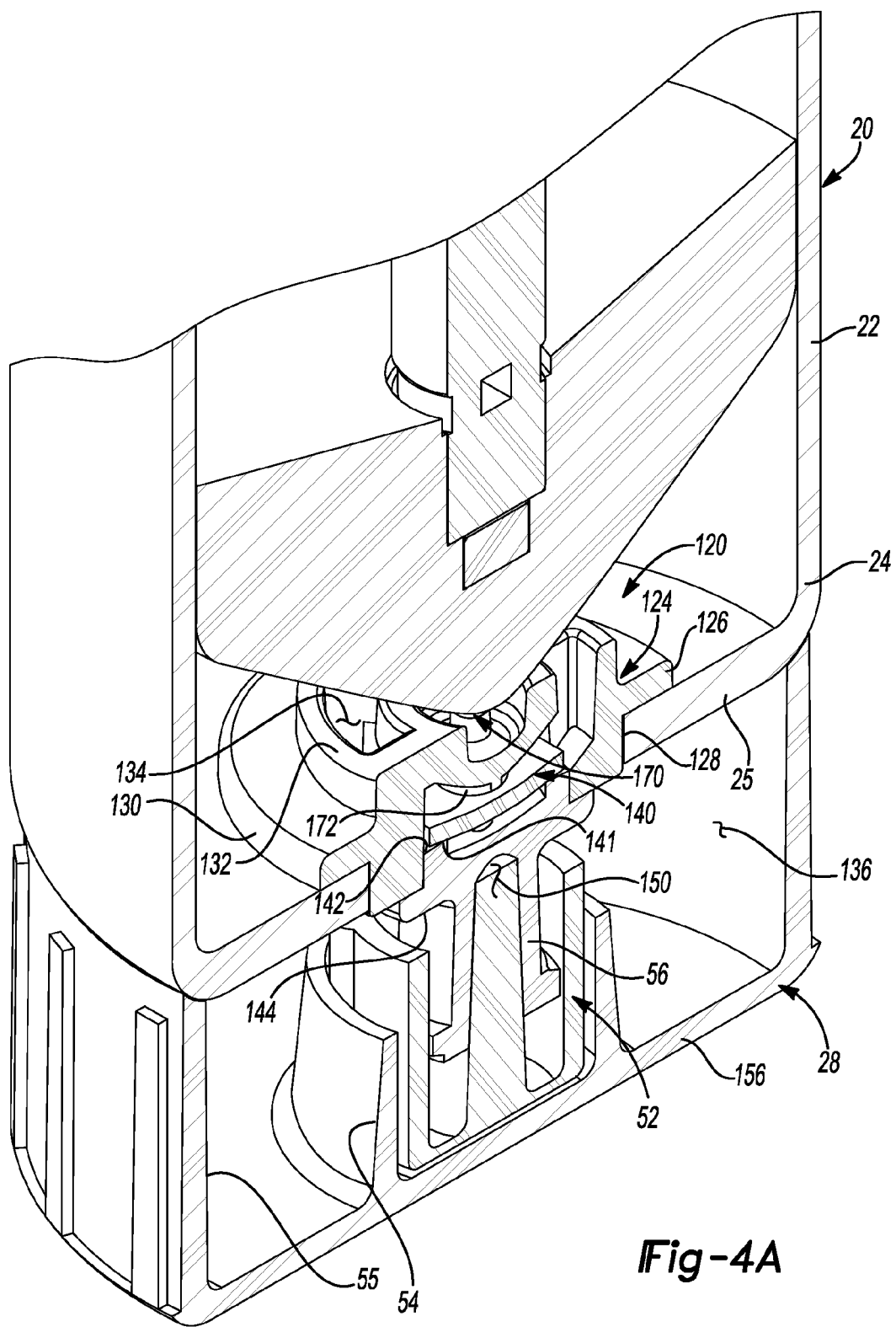
FIG. 4A is a partial cross-sectional view of the separation container.

The valve assembly 120 can include an outer wall or body portion 124 that includes a flange 126 that extends external to an outer wall portion 128 of the valve body 124 to engage the first end wall 25. It will be understood, however, that the valve assembly 120, including the valve body portion 124, can be formed as a single piece with the first end wall 25. However, as illustrated in FIG. 4, the valve assembly 120 can be formed separately and connected to the first end wall 25. Appropriate connections can include adhesives, welding, snap or interference fitting, or any other appropriate connection. The valve body 124 generally will be connected with the first end wall 25 in a substantially liquid tight manner. Accordingly, a fluid positioned within the container 20 will not leak around the valve body 124 to an area external to the container 20. Nevertheless, the valve assembly 120 can be operated to allow a material to be at least placed within the container 20 from a position external to the container 20, as discussed further herein.

With continuing reference to FIGS. 1-3 and additional reference to FIG. 4, the valve body 124 can include the outer wall portion 128 that extends through the first end wall 25 and a second outer wall portion 130 that extends opposite the first outer wall portion 128 on the opposite side of the flange 126. The second outer wall portion 130 can extend to a top portion and a top wall 132 can be defined substantially transverse to the outer wall portion 130. The top wall portion 132 can be a transverse wall and can define passages 134 that extend axially through the valve body 124 from an area exterior to the container 20, such as an area below or outside of the first end wall 25 generally defined as stand enclosed area 136. The area 136, as illustrated in FIG. 4, can be enclosed by a stand or end cap 28 as discussed further herein. Nevertheless, the valve passage 134 can be defined as a passage through the valve body 124 that is closed by a valve or flexible valve member 140. The flexible valve member 140 can seat on an upper edge 142 of a second valve body portion 144 that is interconnected with the valve body 124 and a lower edge 172 of the first valve body 124. The interconnection of the second valve body 144 with the valve body 124 can be any appropriate connection, such as an adhesive, welding, or the like. The second valve body 144 can also be formed as one piece with the luer member 56 or connected thereto.

The check valve member 140 can be formed of any appropriate flexible but sealing material. For example, silicon or other natural or synthetic rubbers can be used as the sealing member 140. Generally the valve or sealing member 140 can be formed of a biocompatible material that will not contaminate a biological material, such as white blood cells, stromal cells, red blood cells, platelets, plasma, or other biological materials. Additionally, the valve member 140 can be flexible without being toxic to a patient.

The flexible valve body 140 can define a valve member or closing portion between the passage 134 defined by the first valve body 124 and a second valve passage 150 defined by the second valve body 144. The second valve passage 150 can be formed through the second valve body 144 where a portion of the second valve body 144 can define the luer fitting 56. It will be understood that other appropriate connections can be provided other than the luer fitting 56, but luer fittings are a generally known connection. The sealing cap or luer cap 52 can be provided to interconnect with the luer fitting 56 to seal or otherwise cover the second valve body 144. The stand 28 can interconnect with the cap 52 by an interference, snap-fit connection, or with glue. The stand 28 can include a bottom wall 156 and the sidewall 55 to contact the first end wall 25 of the container 20. The stand 28, therefore, can assist in holding the container 20 in a substantially vertical position although the second valve body 144 and the luer cap 52 extend and provide a small surface area from the bottom of the container 20. It will be understood that the stand 28 can also be formed integrally or as one piece with the cap 52.

The valve body 124 can also include a boss or contact point 170 to engage the buoy 60, and particularly at a point or bottom surface 92 of the buoy member 62. It will be understood, however, that the surface 132 can be substantially flat save for the passages or passage 134 defined through the valve body 124. The valve assembly 120, therefore, can provide or form a contact surface with the buoy 60 to resist movement of the buoy 60 and to maintain the buoy within the container 20.

The valve member 140 can be fixed within the valve assembly 120 such that it is able to flex relative to the first valve body 124. In particular, the valve member 140 can be a check valve that allows for a material to enter the container 20 while resisting or substantially limiting material removal or movement through the check valve 120 out of the container 20. Therefore, the flexible member can generally include an edge 141, such as an annular or other geometric shaped edge, that engages or contacts an edge 142 of the second body 144. In a relaxed or closed position the check valve member 140 is resting on the edge 142 and substantially closes the valve assembly 120. The valve member 140 can flex towards the surface 132 either completely or at an edge. If only an edge flexes a central portion of the valve member 140 can be held in place by a boss portion 172. Accordingly, the valve member 140 can flex around an edge, such as an annular edge, near the edge 142 of the second valve body 144 to allow material to pass into the container 20, as discussed further herein.

Although, as discussed above, the valve assembly 120 can include at least one valve body portion 144 and/or luer connection 56 that is external to the end wall 25, it will be understood that the end wall 25 may be the external most portion of the container 20. That is, the valve assembly 120 can be formed to seat internally of the end wall 25 such that the external surface of the end wall 25 is flush and/or substantially planar, as illustrated in FIG. 4B.

Figure 4B:
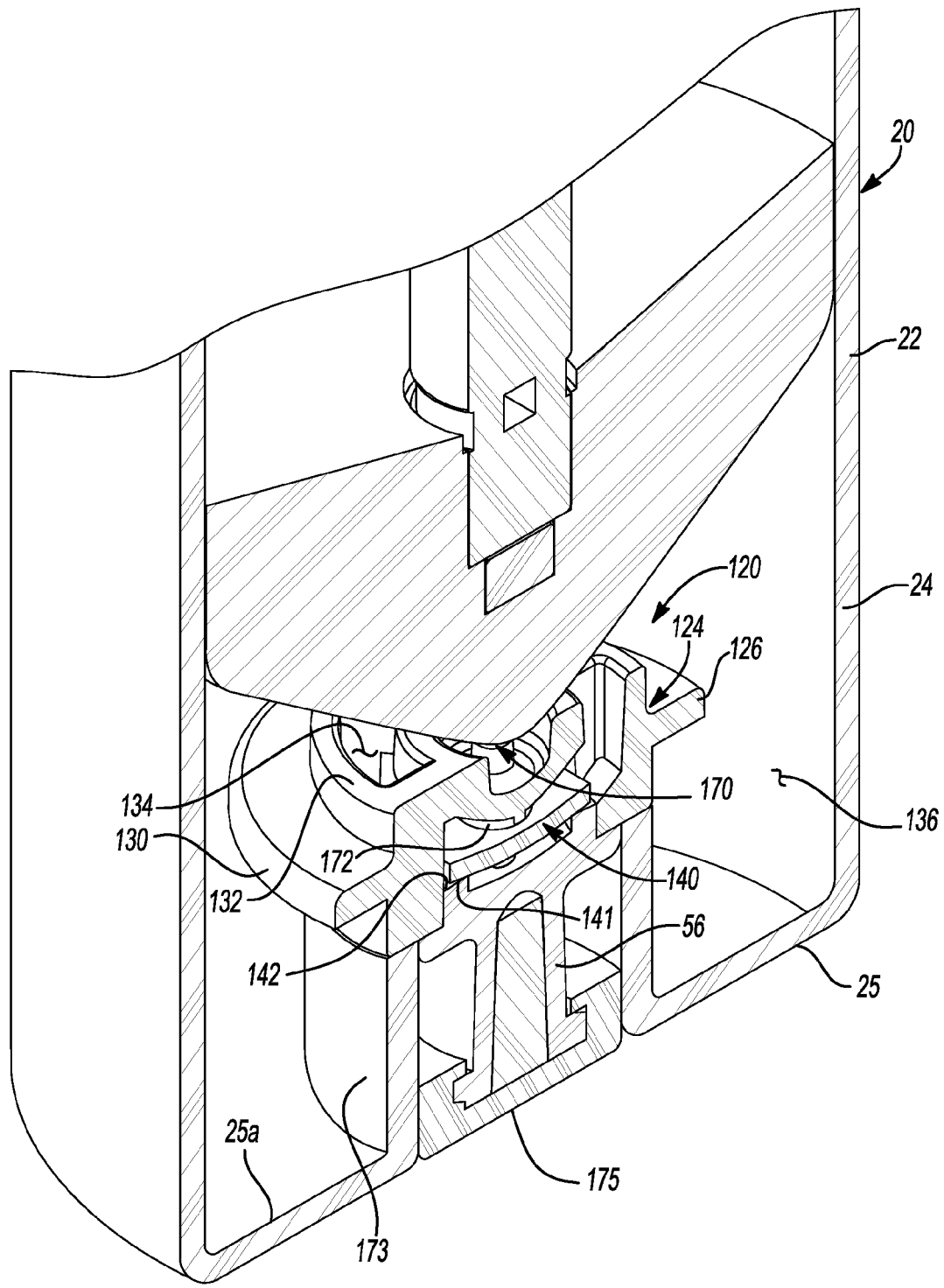
FIG. 4B is a partial cross-sectional view of a separation container according to various embodiments.

In the configuration illustrated in FIG. 4B, the luer connection 56 does not extend externally or away from the end wall 25. The end wall 25 is formed substantially continuously and/or as one piece with the sidewall 22 of the container 20. The luer connection 56 or appropriate connection can be formed to be substantially flush with the end wall 25 as well. As illustrated in FIG. 4B, the stand 28, as a separate and/or additional member, need not be included to support and/or direct forces during centrifugation onto the container 20.

An internal support member or portion 173 can extend from an internal surface 25a of the end wall 25 to engage and/or support at least a portion of the valve assembly 120. For example, the support portion 173 can engage the first valve body 124 or the second valve body 144. The support portion 173 can assist in supporting and holding the valve assembly 120 during use of the device 10, including during centrifugation of the container and/or the whole material. It is understood, therefore, that in various embodiments other container engagement portions, such as the flange 126, can be eliminated from the valve assembly 120. Also, a cap 175 can be used to cap the luer connection 56, if selected. It is understood, however, that the cap 175 is not necessary and that the luer connection 56 can be maintained through the end wall 25 without the cap 175.

According to the various embodiments, the separation assembly that includes the container 20 can be used to separate a material, such as a biological material collected from a patient 178. FIGS. 5-8 illustrate, and are discussed herein, an exemplary method of a use of the container 20. The biological material 188 can include whole blood, bone marrow, adipose tissue, stem cells or multi-potent cells, or other appropriate materials. It is understood that separated materials may also be previously pooled materials. The separation assembly of the container 20 can be used to separate any whole material that can be fractionated, such as with gravity fractionation. Non-biological materials include silts, (e.g. from effluent sources), compound suspensions of industrial waste, etc.

Nevertheless, as illustrated in FIGS. 5-8, the separation container can be used to separate a whole material positioned in a container 20 that is withdrawn from the patient 178. A first syringe 180 can be used to withdraw the whole material or whole materials from the patient 178. For example, whole blood, bone marrow aspirate, or a combination of the two can be withdrawn from the patient 178. The single first syringe 180 can be used to withdraw all of the whole materials from the patient 178 or multiple first syringes 180 can be used to withdraw the whole material and all of the whole materials can be positioned within the container 20 sequentially, such that all of the materials are within the container 20 at the same time. For example, whole blood can be withdrawn with the first syringe 180. Also, bone marrow can be aspirated with the same or different first syringe 180a for filling into the container 20.

With reference to FIG. 6, the syringe 180 can interconnect with the luer 56 of the container 20. A plunger 184 of the syringe 180 can be moved generally in the direction of arrow 186 to force the whole material 188 through the valve assembly 120 into the container 20 generally in the direction of arrow 192. When the whole material 188 is being moved in the direction of arrow 192, the valve member 140 can flex away from the valve seat or edge 142 of the second valve body 144 to allow the whole material 188 to pass through the passage 134 of the valve assembly 120. This can allow the container 20 to fill between the first buoy member 62 and the first end wall 25. The buoy 60 can move or be pushed by the whole material 188 as the whole material 188 is moved into the container 20. It is understood, however, that a volume of the whole material 188 may be greater than that of a volume between the buoy 62 and the first end wall 25 of the container 20, especially when the buoy 60 contacts the stop legs 96a-c. Accordingly, a certain volume of material 188 can be forced to pass the buoy member 62, according to various embodiments. It can be selected, however, but is not required to form a seal between the first buoy member 62 towards the second end 26 while being filled and the container 20 such that material will not pass the buoy 60 and that the container 20 will only be filled between the first buoy member 62, or the exterior surface thereof, and the first end wall 25.

Once the container 20 is filled with the selected volume of the whole material 188, which can include a combination of material such as whole blood and bone marrow, the stand 28 can be interconnected with the container 20. As discussed above, the stand 28 can be adhered, such as with glue, or have an interference fit with the cap that is positioned over the luer 56. The stand 28 allows the luer 56 to extend out of the first end wall 25 while maintaining a selected external diameter, such as to fit within a bucket of a centrifuge. Centrifuge assemblies can include an appropriate centrifuge assembly, such as model 755VES centrifuge sold by The DRUCKER COMPANY of Philipsburg, Pa. The stand 28, however, is not required as the check valve assembly can be contained within the container 20 and an opening or flush portion can be provided through the first end wall 25. The stand 28 can support the container within the centrifuge, such as a bucket of the centrifuge to transfer forces to the wall 22 of the container 20. Alternatively, or in addition thereto, the stand 28 can be fixed or formed as one member with the container 20 such that the valve assembly is contained within the stand 28 and a flush opening is provided through the bottom wall 156 of the stand. If the stand 28 is formed as one piece with the container 20 the configuration may be similar to that illustrated in FIG. 4B.

A centrifuge, as is generally understood, can spin the container 20 including the whole material to increase gravitational force within the container 20 to allow for gravitational separation of the whole material 188 based upon the specific gravities or densities of the various components of the whole material. In the centrifuge the gravitational forces are generally applied along a longitudinal axis 20a of the container 20 and towards the first end 24 such that the most dense material is urged towards the first end wall 25 and the port 56. The centrifugation, therefore, causes fractionation of the whole material 188 that is positioned within the container 20. Because the container 20 is filled first between the first end wall 25 and the buoy 60, the container 20 can be positioned in the centrifuge such that the bottom or first end wall 25 is positioned furthest away from a center of rotation. It is understood, as discussed and illustrated in FIG. 7, that some whole material 188 can pass the buoy system 60 during filling. Nevertheless, denser material portions will collect or fractionate nearest the first end wall 25 or at the bottom of the container 20 when positioned in a centrifuge device such that the first end wall is positioned away from the center of rotation of the centrifuge device.

Figure 8:
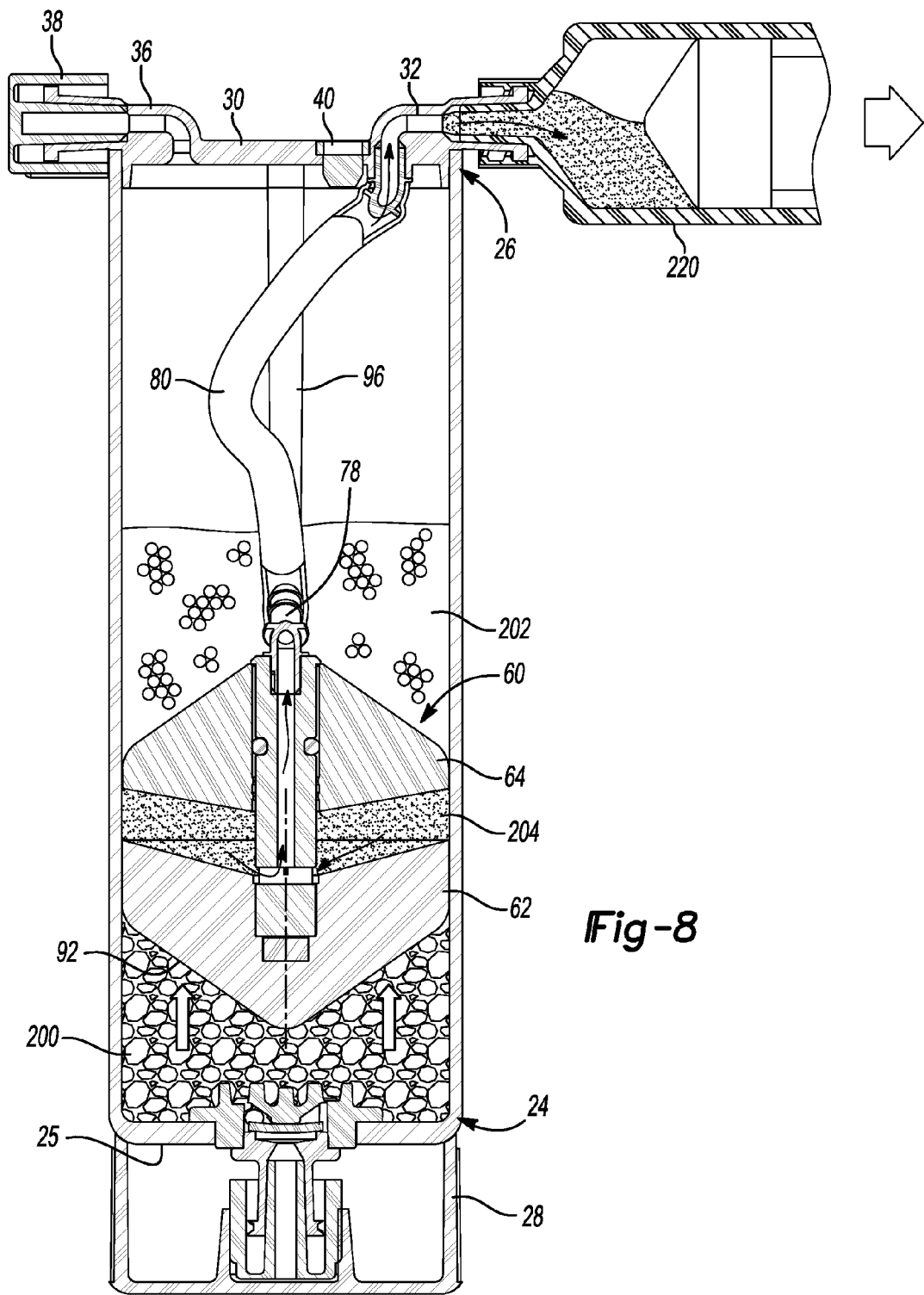
FIG. 8 is a cross-sectional view of a whole material that has been separated where at least a component thereof is being withdrawn from the separation container.

As exemplarily illustrated in FIG. 8, the fractionated whole material, such as whole blood, bone marrow aspirate, or a combination thereof, can include a first fraction 200 of material generally with a density greater than 1.06 g/cc, such as red blood cells, bone spicules, or blood and marrow clots nearest the first end wall 25. The lightest fraction or second fraction 202 can include plasma and other like components of whole blood, bone marrow aspirate, or a combination thereof. A middle or third fraction 204 can include buffy coat including platelets, white blood cells, stromal cells, and other components of whole blood, bone marrow aspirate, or a combination thereof. Since the red blood cells and other dense components are maintained between the buoy 60 and the first end wall 25 any globules of coagulated materials will not interfere with the specific gravity or density of the buoy system 60. For example, any clot that may form in the whole blood, bone marrow aspirate, or a combination thereof, will not interfere with movement of the buoy 60 within the container 20. If a clot contacts the buoy 60 on or around a second buoy component 64 as the buoy 60 attempts to move through the container 20, due to the specific gravity of the buoy 60 relative to the fractioned materials, the clot may alter the effective gravity of the buoy 60 by contacting and sticking to at least the second buoy component 64 and increasing its respective density. The clot, however, in the separation container 20, will remain between the first end wall 25 and the buoy 60 and therefore substantially not interact with the buoy 60 or alter the effective density of the buoy 60. Accordingly, the separation can fractionate the whole material and not be affected by components of the whole material that may alter the density of the buoy 60. Thus, the buoy 60 maintains or substantially maintains its original and intended density throughout the separation. Further, the buoy 60 need not act as an agitator to achieve the selected separation of the whole material based on the gravity separation. After separation, as illustrated in FIG. 8, a second syringe 220 can interconnect with the withdrawal or removal port 32 to withdraw material through the withdrawal tube 80 that is interconnected with the buoy 60 via the port 78 thus the third fraction, such as the buffy coat 204 that is positioned within the separation volume of the buoy 60 can be withdrawn from the second end 26 of the container 20 and the cap 30 that is opposite the first end 24. Thus, a material will be withdrawn from the container 20 at an end that is opposite the first end 24. Therefore, as illustrated in FIG. 6, the container 20 can be filled through the first end 24, such as via the valve assembly 120, and withdrawn from the second end 26 that is opposite the first end 24 and also on an opposite side of the buoy 60, as illustrated in FIG. 8.

Also, materials can be withdrawn through the cap 30 using either of the ports 32 or 36. For example, the port 32 can be used to draw material 204 from between the two members of the buoy 60. Also, the second port 36 can be used to withdraw material 202 from between the buoy 60 and the cap 30.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to separate a whole material including multiple components, comprising:
    a container having an external wall defining a container volume within the external wall and extending along a long axis between a first end and a second end of the container;
    a separation buoy moveable within the container volume between the first end and the second end, the separation buoy comprising at least one of a selected specific gravity and density to move the separation buoy in the whole material to a selected location within the container upon fractionation of the whole material by centrifugation;
    a first fill port at the first end of the container;
    a valve assembly formed within the first fill port and comprising a valve body including a boss configured to support the separation buoy and defining at least one passage adjacent the boss;
    a second withdrawal port at the second end of the container; and
    a stand including:
        a stand end wall for supporting the container on a surface,
        an outer stand wall extending from the stand end wall to engage at least one of the first end or the external wall of the container to enclose the first fill port, wherein the outer stand wall has an outer dimension that is substantially equivalent to an outer dimension of the external wall of the container, and an inner stand wall extending from the stand end wall to engage the first fill port;
    wherein the first fill port is configured to receive the whole material into the container and the second withdrawal port is configured to permit withdrawal of at least a selected component of the whole material from the container through the second withdrawal port.

2. The system of claim 1, wherein the valve assembly includes a check valve assembly formed within the first fill port having a flexible valve member and a valve seat, wherein an edge of the flexible valve member is moveable from a closed position when the flexible valve member sealingly engages the valve seat to an open position when the edge of the flexible valve member at least partially disengages the valve seat;
    wherein the boss engages a central portion of the flexible valve member to hold the valve member in place.

3. The system of claim 1, wherein the first end includes a first end wall;
    wherein the first fill port includes an extension portion that extends beyond the first end wall.

4. The system of claim 1, wherein the separation buoy substantially physically separates the first end of the container from the second end of the container;
    wherein the first fill port at the first end of the container is positioned in the container relative to the separation buoy to minimize interference of a coagulated material during an operation of the separation buoy.

5. The system of claim 4, wherein the separation buoy includes at least a first buoy member and a second buoy member configured to define a separation volume between the first buoy member and the second buoy member;
    wherein the second withdrawal port is in fluid communication with the separation volume to remove a selected fraction from the container through the second withdrawal port, where the second withdrawal port is separated from the first fill port by at least one of the first buoy member or the second buoy member.

6. The system of claim 1, wherein the stand operably engages the first end of the container to support the container in a centrifuge device during centrifugation of the container.

7. The system of claim 1, wherein the first end includes a first end wall;
    wherein the first fill port is substantially flush with the first end wall.

8. The system of claim 1, wherein the separation buoy includes at least a first buoy member and a second buoy member;
    wherein the first buoy member includes a first wall having a steep angle to ease passage of at least a portion of the whole material past the separation buoy within the container.

9. The system of claim 1, further comprising:
    a cap configured to interconnect with the first fill port;
    wherein the inner stand wall engages the cap when the stand is coupled to the container.

10. A system to separate a whole material including multiple components, comprising:
    a container having an external wall defining a container volume within the external wall and extending along a long axis between a first end and a second end of the container;
    a separation buoy positioned within the container volume between the first end and the second end;

a first fill port at the first end of the container having a connection that extends beyond the first end of the container;

a check valve assembly formed within the first fill port, the check valve assembly having a flexible valve member, a valve seat, and a valve body including a boss and defining at least one passage adjacent the boss, wherein an edge of the flexible valve member is moveable from a closed position when the flexible valve member sealingly engages the valve seat to an open position when the edge of the flexible valve member at least partially disengages the valve seat, wherein the boss configured to support the separation buoy and engage a central portion of the flexible valve member to hold the valve member in place;

a second withdrawal port at the second end of the container; and a stand including:
- a stand end wall for supporting the container on a surface,
- an outer stand wall extending from the stand end wall to engage at least one of the first end or the external wall of the container to enclose the first fill port, wherein the outer stand wall has an outer dimension that is substantially equivalent to an outer dimension of the external wall of the container, and
- an inner stand wall extending from the stand end wall to engage the first fill port;

wherein the first fill port is configured to receive the whole material into the container and the second withdrawal port is configured to permit withdrawal of at least a selected component of the whole material from the container through the second withdrawal port.

11. The system of claim 10, wherein the separation buoy includes a buoy density of about 1.01 grams per cubic centimeter to about 1.10 grams per cubic centimeter.

12. The system of claim 11, wherein the separation buoy includes a first buoy member and a second buoy member combined to include the buoy density.

13. The system of claim 10, wherein the separation buoy substantially physically separates the first end of the container from the second end of the container.

14. The system of claim 10, wherein the stand operably engages the first end of the container to support the container in a centrifuge device during centrifugation of the container.

15. The system of claim 10, wherein the first end includes a first end wall;
wherein the first fill port is substantially flush with the first end wall.

16. The system of claim 10, wherein the separation buoy includes at least a first buoy member and a second buoy member;
wherein the first buoy member includes a first wall having a steep angle to ease passage of at least a portion of the whole material past the separation buoy within the container.

17. The system of claim 10, further comprising:
a cap configured to interconnect with the first fill port;
wherein the inner stand wall engages the cap when the stand is coupled to the container.

* * * * *